US010299689B2

(12) United States Patent
Ong et al.

(10) Patent No.: US 10,299,689 B2
(45) Date of Patent: May 28, 2019

(54) SYSTEM AND METHOD OF DETERMINING A RISK SCORE FOR TRIAGE

(71) Applicant: Singapore Health Services Pte Ltd, Singapore (SG)

(72) Inventors: Marcus Eng Hock Ong, Singapore (SG); Nan Liu, Singapore (SG)

(73) Assignee: SINGAPORE HEALTH SERVICES PTE LTD, Singapore (SG)

( * ) Notice: Subject to any disclaimer, the term of this patent is extended or adjusted under 35 U.S.C. 154(b) by 748 days.

(21) Appl. No.: 14/773,747

(22) PCT Filed: Mar. 7, 2014

(86) PCT No.: PCT/SG2014/000110
§ 371 (c)(1),
(2) Date: Sep. 8, 2015

(87) PCT Pub. No.: WO2014/137295
PCT Pub. Date: Sep. 12, 2014

(65) Prior Publication Data
US 2016/0022162 A1 Jan. 28, 2016

Related U.S. Application Data

(63) Continuation of application No. 13/791,764, filed on Mar. 8, 2013, now Pat. No. 9,775,533.

(51) Int. Cl.
*A61B 5/04* (2006.01)
*A61B 5/024* (2006.01)
(Continued)

(52) U.S. Cl.
CPC ........ *A61B 5/04012* (2013.01); *A61B 5/0205* (2013.01); *A61B 5/02055* (2013.01);
(Continued)

(58) Field of Classification Search
CPC .............. A61B 2505/03; A61B 5/0205; A61B 5/02055; A61B 5/02405; A61B 5/04012;
(Continued)

(56) References Cited

U.S. PATENT DOCUMENTS

2010/0217144 A1* 8/2010 Brian ................... A61B 5/0452
600/523

FOREIGN PATENT DOCUMENTS

WO WO 2009005734 8/2009

OTHER PUBLICATIONS

Nitesh V. Chawla et al.: "SMOTE: Synthetic Minority Over-sampling Technique," Journal of Artificial Intelligence Research, vol. 16 Jan. 1, 2002 (Jan. 1, 2002), pp. 321-357.

(Continued)

*Primary Examiner* — Amanda K Hulbert
(74) *Attorney, Agent, or Firm* — Hultquist, PLLC; Steven J. Hultquist

(57) ABSTRACT

The present disclosure provides a system and method of determining a risk score for triage. In particular, a system is provided for providing an assessment of risk of a cardiac event for a patient, for example an incoming patient to a hospital emergency department complaining of chest pain. In the disclosure, the system includes an input device for measuring physiological data based vital signs parameter of the patient, a twelve-lead electrocardiogram (ECG) device for establishing an ECG obtained from results of the electrocardiography procedure, and determining an ECG parameter and a heart rate variability (HRV) parameter therefrom. An ensemble-based scoring system is further provided, establishing weighted classifier based on past patient data and where the vital signs parameter, the ECG parameter and the HRV parameter are compared to corresponding weighted (Continued)

classifiers to determine a risk score. A corresponding method to determine a risk score for triage is also provided.

18 Claims, 11 Drawing Sheets

(51) Int. Cl.

| | |
|---|---|
| *A61B 5/0452* | (2006.01) |
| *A61B 5/0205* | (2006.01) |
| *A61B 5/00* | (2006.01) |
| *A61B 5/0408* | (2006.01) |
| *A61B 5/0456* | (2006.01) |
| *A61B 5/046* | (2006.01) |
| *A61B 5/0468* | (2006.01) |
| *A61B 5/0472* | (2006.01) |
| *A61B 5/1455* | (2006.01) |
| *G16H 50/30* | (2018.01) |
| *G06F 19/00* | (2018.01) |

(52) U.S. Cl.
CPC .......... *A61B 5/02405* (2013.01); *A61B 5/046* (2013.01); *A61B 5/0408* (2013.01); *A61B 5/0452* (2013.01); *A61B 5/0456* (2013.01); *A61B 5/0468* (2013.01); *A61B 5/0472* (2013.01); *A61B 5/14552* (2013.01); *A61B 5/4824* (2013.01); *A61B 5/7275* (2013.01); *G06F 19/00* (2013.01); *G16H 50/30* (2018.01); *A61B 2505/03* (2013.01)

(58) Field of Classification Search
CPC ... A61B 5/0408; A61B 5/0452; A61B 5/0456; A61B 5/046; A61B 5/0468; A61B 5/0472; A61B 5/14552; A61B 5/4824; A61B 5/7275; G06F 19/00; G16H 50/30
USPC .......................................................... 600/508
See application file for complete search history.

(56) References Cited

OTHER PUBLICATIONS

Luis Mena et al.: "Machine Learning for Imbalabced Datasets: Application in Medical Diagnostic," Jan. 1, 2006 (Jan. 1, 2006).
Suzan Kaknar-Tezel et al.: " Improving SVM classification on imbalance time series data sets with ghost points," Knowledge and Information System; An International Journal, Springer-Verlag, Lo, vol. 28, No. 1, Jun. 16, 2010 (Jun. 16, 2010).
Anima Singh et al.: "A comparison of non-symmetric entropy-based claissification trees and support vector machine for cardiovascular risk stratification" Engineering in Medicine and Biology Society, EMBC, 2011 Annual International Conference of the IEEE, IEEE, Aug. 30, 2001 (Aug. 30, 2011), pp. 79-82.
Nan Liu et al.: "An Intelligent Scoring System and Its Application tp Cardiac Arrest Prediction," IEEE Transactions on Information Technology in Biomedicine, IEE Service Center, Los Alamitos, CA, US. vol. 16, No. 6, Nov. 1, 2012 (Nov. 1, 2012).
International Search Report, dated Jun. 10, 2014 for corresponding International Application No. PCT/SG2014/000110.
Written Opinion of the ISA, dated Jun. 10, 2014 for corresponding International Application No. PCT/SG2014/000110.
Luis Mena et al.: "Machine Learning for lmbalabced Datasets: Application in Medical Diagnostic," Jan. 1, 2006 (Jan. 1, 2006).

* cited by examiner

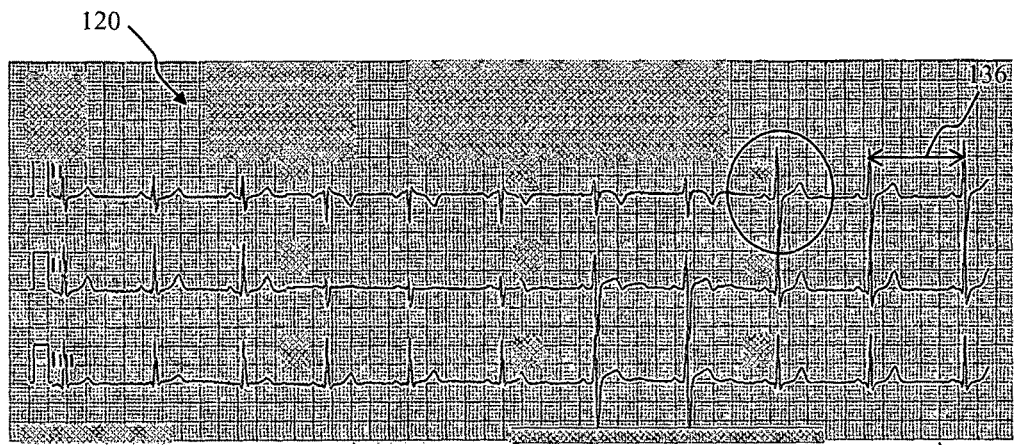
FIG. 3A
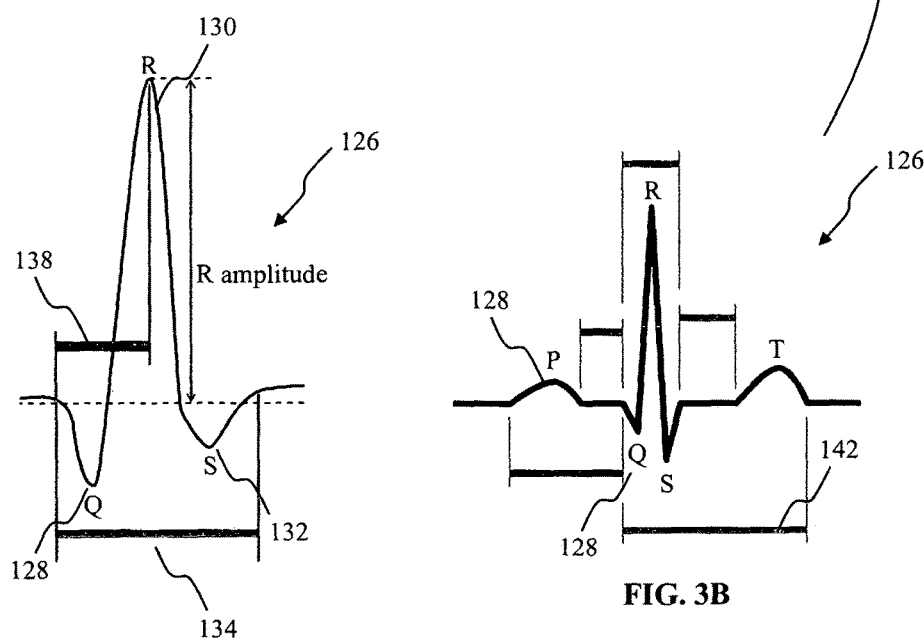
FIG. 3C
FIG. 3B

SYSTEM AND METHOD OF DETERMINING A RISK SCORE FOR TRIAGE

TECHNICAL FIELD

The present disclosure relates generally to a system and a method of determining a risk score for triage. More particularly, embodiments of the present disclosure are directed to systems and techniques of determining a cardiac risk score, such as for a hospital emergency department, ambulance, clinic, ward, intensive care unit (ICU) or home, based on measurements and readings taken.

BACKGROUND

Patients seen at the emergency department (ED) of a hospital complaining of chest pain have varying levels of complication risk in the acute phase of treatment, usually identified as the first 72 hours from when the affliction first occurs. Similarly, cardiac risk screening and monitoring is often done in ambulances, clinics, wards, ICUs and even from home. In the ED, triage is carried out to assess the severity of the incoming patient's condition and to assign appropriate treatment priorities. Early stratification of risk improves treatment strategies as well as assists with the formulation of proper monitoring for the patient. Risk stratification is necessary in EDs as medical resources, such as doctors, nurses, monitoring systems, monitored beds, resuscitation facilities, intensive care units, etc., are never sufficient for all incoming patients to be attended to instantaneously. For example, in the United States, approximately 6 million patients present with chest pain to the ED each year, which makes chest pain one of the leading principle diagnoses during ED visits. Similarly, early identification of high risk patients can benefit management in ambulances, clinics, wards, ICUs and even for home monitoring. Chest pain severity ranges from self-limited to severe and life threatening situations such as cardiac arrest and lethal arrhythmias. The need to identify high-risk patients allows for timely intervention for preventable and treatable complications.

In the past few decades, scoring systems have also been developed, and are now widely used in intensive care units (ICUs) to predict clinical outcomes and assess the severity of illnesses.

Some of the systems which have been developed are for example, Acute Physiology and Chronic Health Evaluation (APACHE), Simplified Acute Physiology Score (SAPS) and Mortality Probability Model (MPM). Each scoring system has a specific purpose and its own range of applications. For example, risk of death, organ dysfunction assessment and severity of illnesses are possible outcomes of some of these scoring systems.

The development of scoring systems relies on the appropriate selection of variables or parameters with which prediction outcomes are associated. Present triage tools and risk-stratification systems for patients with suspected acute coronary syndromes (ACS) are based on a combination of traditional clinical factors such as patient medical history, cardiac bio markers, and measurements obtained from ED incoming patient screenings, for example observing and obtaining traditional vital signs such as heart rate, respiratory rate, blood pressure, temperature, and pulse oximetry. However, these parameters have not been shown to correlate well with short or long-term clinical outcomes.

Presently, although thrombolysis in myocardial infarction (TIMI) risk score is currently the most clinically accepted risk categorization of patients with ACS, its prediction accuracy is debatable and perhaps somewhat controversial. There are as such limitations to current risk scores for prediction of cardiovascular complications, whilst at the same time, clinical judgment is subjective, as well as being hampered by a limitation in doctoral resource.

SUMMARY

A system is provided for determining a risk score (e.g. for triage), including: a first input device for measuring a first input parameter relating to physiological data of a patient, the first input parameter including a vital signs parameter; a twelve-lead electrode electrocardiogram (ECG) device, for carrying out a electrocardiography procedure on the patient, and establishing an ECG obtained from results of the electrocardiography procedure, the ECG device including an ECG extraction module to extract at least one ECG parameter from the ECG; a heart rate variability (HRV) analysis module for determining a HRV analysis from the ECG, the HRV analysis including at least one HRV parameter; and an ensemble-based scoring system, including: a plurality of weighted classifiers for providing a risk score calculation, the plurality of weighted classifiers established based on past patient data in a database of accumulated past patient data; and an analysis module for receiving the first input parameter, the at least one HRV parameter, and the at least one ECG parameter which are communicated or transmitted to the ensemble-based scoring system, wherein the analysis module determines a risk score by comparing the first input parameter, the at least one HRV parameter, and the at least one ECG parameter to corresponding weighted classifiers.

BRIEF DESCRIPTION OF DRAWINGS

Embodiments of the present disclosure are explained, by way of example, and with reference to the accompanying drawings. It is to be noted that the appended drawings illustrate only examples of embodiments of this disclosure and are therefore not to be considered limiting of its scope, for the disclosure may admit to other equally effective embodiments.

FIG. 3A illustrates a sample ECG printout as provided by the triage system of the present embodiment.

FIG. 3B illustrates a close up of a cardiac cycle from the ECG of FIG. 3A.

FIG. 3C illustrates a close up of the QRS complex of the cardiac cycle of FIG. 3B.

DETAILED DESCRIPTION

Figure 1:
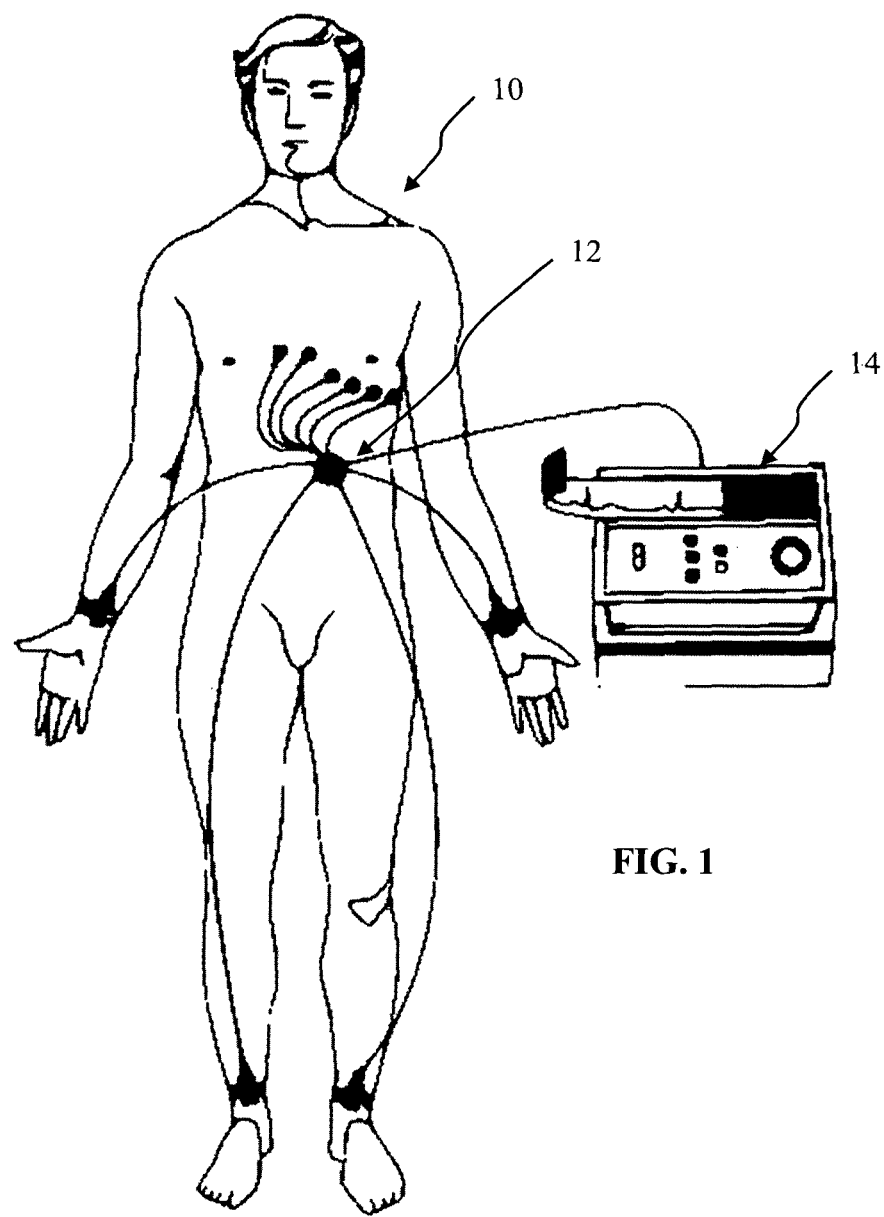
FIG. 1 illustrates a patient connected to a 12-lead ECG.

In the following, reference is made to embodiments of the disclosure. However, it should be understood that the disclosure is not limited to specific described embodiments. Instead, any combination of the following features and elements, whether related to different embodiments or not, is contemplated to implement and practice the disclosure.

Furthermore, in various embodiments the disclosure provides numerous advantages over the prior art. However, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the appended claims except where explicitly recited in a claim(s). Likewise, any reference to "the invention" shall not be construed as a generalization of any inventive subject matter disclosed herein and shall not be considered to be an element or limitation of the appended claims except where explicitly recited in a claim(s).

In an aspect of the present disclosure, there is provided a system for determining a risk score for triage or for other environments/situations, the system including a first input device for measuring a first input parameter relating to physiological data of a patient, the first input parameter including a vital signs parameter; a twelve-lead electrode electrocardiogram (ECG) device, for carrying out a electrocardiography procedure on the patient, and establishing an ECG obtained from results of the electrocardiography procedure, the ECG device including an ECG extraction module to extract at least one ECG parameter from the ECG; a heart rate variability (HRV) analysis module for determining a HRV analysis from the ECG, the HRV analysis including at least one HRV parameter; and an ensemble-based scoring system, including: a plurality of weighted classifiers for providing a risk score calculation, the plurality of weighted classifiers established based on past patient data in a database of accumulated past patient data; and an analysis module for receiving the first input parameter, the at least one HRV parameter, and the at least one ECG parameter which are communicated or transmitted to the ensemble-based scoring system, wherein the analysis module determines a risk score by comparing the first input parameter, the at least one HRV parameter, and the at least one ECG parameter to corresponding weighted classifiers.

Such a system can provide a prompt insight suitable for use in a hospital emergency department, ambulance, clinic, ward, intensive care unit (ICU) or home in providing a classification as to the severity of a cardiac event situation for an incoming patient. The present system caters to the utilization of a combination of a vital signs parameter, a ECG parameter and a HRV parameter, which has been proposed after much study and research by the present inventors to provide a possibly clearer insight as to the identification of risk of an acute coronary syndrome. A 12-lead ECG is also proposed for usage in preference to the high level of detail and insight such a procedure provides.

Furthermore the present system provides for an ensemble-based scoring system, which is inherently an intelligent artificial neural network, capable of learning and training from past data to establish classifiers that are weighted based on a derived understanding of which parameters contribute to a higher occurrence or severity of cardiac events, and for comparison with present input parameters to determine a risk score as to triage.

According to an embodiment, the at least one ECG parameter is any one of a ST elevation, a T wave inversion, a Q wave, a QT interval correction (QTc), a QRS axis, a left bundle branch block (BBB), a right BBB, an IntraVentricular Conduction Delay (IVCD), a left atrial abnormality (LAA), a left ventricular hypertrophy (VH), a right VH, and an atrial fibrillation.

According to an embodiment, the HRV analysis module further includes a time domain analysis module for determining the at least one HRV parameter from a plurality of RR intervals extracted from the ECG.

According to an embodiment, the at least one HRV parameter is any one of an average length of the RR intervals, standard deviation of all RR intervals, a mean heart rate, a standard deviation of all instantaneous heart rate values, a NN50 count, a pNN50 percentage, a square root of mean squared differences of successive RR intervals, a HRV triangular index, and a baseline width of triangular fit into a RR interval histogram.

According to an embodiment, the HRV analysis module further includes a frequency domain analysis module for determining the at least one HRV parameter from a plurality of RR intervals extracted from the ECG.

According to an embodiment, the at least one HRV parameter is any one of a total power, a very low frequency power, a low frequency power (LF), a high frequency power (HF), a normalized low frequency power, a normalized high frequency power, and a ratio of LF/HF.

According to an embodiment, the first input device is any one of a heart rate monitor, a respiratory rate monitor, a blood pressure monitor, an oximeter, and a dolorimeter.

According to an embodiment, there is provided a second input device for establishing a second input parameter relating to a medical status of the patient, the second input parameter received by the analysis module, and wherein the analysis module determines the risk score by further comparing the second input parameter to a corresponding weighted classifier.

According to an embodiment, the ensemble-based scoring system further includes a data access module for obtaining past patient data and configured for data communication with the database of accumulated past patient data.

According to an embodiment, the ensemble-based scoring system further includes a sorting module arranged to receive data from the database of accumulated past patient data; and sort the data into a plurality of data sets, each data set corresponding to a classifier, and including an imbalanced data set.

According to an embodiment, the ensemble-based scoring system further includes a sampling module arranged to receive a first imbalanced data set corresponding to a first classifier, including a first majority data set including a first number of data samples, and a first minority data set including a second number of data samples, from the sorting module; and extract a first majority data subset including a third number of samples from the first majority data set; wherein the third number of samples in the first majority data subset is equal to the second number of samples in the first minority data set.

According to an embodiment, the ensemble-based scoring system further includes a classifier generation module for establishing the plurality of weighted classifiers, based on past patient data provided by the data access module.

According to an embodiment, the classifier generation module further includes a training module arranged to receive the first majority data subset and the first minority data set from the sampling module; and build a first classification model to represent the first classifier with the first majority data subset and the first minority data set.

According to an embodiment, the training module receives a plurality of majority data subsets and minority data sets from the sampling module; and builds classification models representing a plurality of classifiers with the received plurality of majority data subsets and minority data sets.

According to an embodiment, the classifier generation module further includes a weighing module for allocating each of the plurality of classifiers with an equal weightage, to obtain the plurality of weighted classifiers.

According to an embodiment, the training module includes a support vector machine to build the classification model.

According to an embodiment, the ensemble-based system further includes an over-sampling module arranged to receive the first majority data subset and the first minority data set from the sampling module; and create a first synthetic data set by applying a process of synthetic over-sampling with replacement on the first majority data subset and the first minority data set.

According to an embodiment, the over-sampling module over-samples the first minority data set by taking a data point in the first minority data set and introduces synthetic examples along a line segment joining the data point to a predetermined number of data point neighbors.

According to an embodiment, the ensemble-based system further includes a validation module arranged to: build a first classification model with a training module based on the first majority data subset and the first minority data set corresponding to the first classifier; validate the first classification model against the first synthetic data set; and obtain a resultant prediction accuracy of the first classification model, representing the importance of the first classifier.

According to an embodiment, the over-sampling module receives a plurality of majority data subsets and minority data sets from the sampling module and creates a plurality of synthetic data sets; the training module builds a plurality of classification models representing a plurality of classifiers with the received plurality of majority data subsets and minority data sets; the validation module validates the plurality of classification models against the plurality of synthetic data sets, and obtains a plurality of prediction accuracies of the classification models, representing the importance of each of the plurality of classifiers.

According to an embodiment, the classifier generation module further includes a weighing module for allocating each of the plurality of classifiers with a weightage according to its importance, to obtain the plurality of weighted classifiers.

According to an embodiment, the analysis module further includes a testing module arranged to: receive any of the first input parameter, the at least one HRV parameter, and the at least one ECG parameter; evaluating the parameter with its corresponding weighted classifier; and generate a binary prediction output of either 0 or 1 for each evaluated weighted classifier.

According to an embodiment, the analysis module further includes a scoring module for calculating the risk score based on a normalized summation of the binary prediction outputs of all evaluated weighted classifiers.

According to a second aspect of the present disclosure, there is provided a method of determining a risk score for triage, including: measuring a first input parameter relating to physiological data of a patient, the first input parameter including a vital signs parameter; carrying out a twelve-lead electrocardiography procedure on the patient; establishing an ECG (providing ECG information, signals or data) from results of the electrocardiography procedure, the ECG including at least one ECG parameter extractable from the ECG; extracting the at least one ECG parameter from the ECG; determining a heart rate variability (HRV) analysis from the ECG, the HRV analysis including at least one HRV parameter; providing the first input parameter, the second input parameter, the at least one HRV parameter, and the at least one ECG parameter to an ensemble-based scoring system; the ensemble-based scoring system including a plurality of weighted classifiers for providing a risk score calculation, the plurality of weighted classifiers established based on past patient data in a database of accumulated past patient data; and determining a risk score with the ensemble-based scoring system by comparing the first input parameter, the at least one HRV parameter, and the at least one ECG parameter to corresponding weighted classifiers.

According to an embodiment, the at least one ECG parameter is any one of a ST elevation, a T wave inversion, a Q wave, a QT interval correction (QTc), a QRS axis, a left bundle branch block (BBB), a right BBB, an IntraVentricular Conduction Delay (IVCD), a left atrial abnormality (LAA), a left ventricular hypertrophy (VH), a right VH, and an atrial fibrillation.

According to an embodiment, the method includes extracting a plurality of RR intervals from the ECG and performing any one of a time domain analysis and a frequency domain analysis to obtain the at least one HRV parameter.

According to an embodiment, the at least one HRV parameter is any one of an average length of the RR intervals, standard deviation of all RR intervals, a mean heart rate, a standard deviation of all instantaneous heart rate values, a NN50 count, a pNN50 percentage, a square root of mean squared differences of successive RR intervals, a HRV triangular index, a baseline width of triangular fit into a RR interval histogram, a total power, a very low frequency power, a low frequency power (LF), a high frequency power (HF), a normalized low frequency power, a normalized high frequency power, and a ratio of LF/HF.

According to an embodiment, the first input parameter is any one of a heart rate, a respiratory rate, a blood pressure reading, a temperature reading, a Glasgow Coma Score (GCS), an oxygen saturation reading, and a pain score.

According to an embodiment, the method includes establishing a second input parameter relating to a medical status of the patient, providing the second input parameter to the ensemble-based scoring system, and determining the risk score by further comparing the second input parameter to a corresponding weighted classifier.

According to an embodiment, the second input parameter is any one of a medical history, a drug history, a smoking history, a family history of heart disease, and a number of angina events in the past 24 hours.

According to an embodiment, the method includes obtaining the third set of input parameters from a twelve-lead electrocardiography procedure of at least 5 minutes.

According to an embodiment, the method includes obtaining past patient data with a data access module, the data access module configured for data communication with the database of accumulated past patient data.

According to an embodiment, the method includes: receiving data from the database of accumulated past patient data; and sorting the data into a plurality of data sets, each data set corresponding to a classifier, and including an imbalanced data set.

According to an embodiment, the method includes receiving a first imbalanced data set corresponding to a first classifier, including a first majority data set including a first number of data samples, and a first minority data set including a second number of data samples, from the sorting module; and extracting a first majority data subset including a third number of samples from the first majority data set; wherein the third number of samples in the first majority data subset is equal to the second number of samples in the first minority data set.

According to an embodiment, the method includes establishing the plurality of weighted classifiers with a classifier generation module and based on past patient data provided by the data access module.

According to an embodiment, receiving the first majority data subset and the first minority data set from the sampling module with a training module; and building a first classification model to represent the first classifier with the first majority data subset and the first minority data set.

According to an embodiment, the method includes: receiving, with the training module, a plurality of majority data subsets and minority data sets from the sampling module; and building classification models representing a plurality of classifiers with the received plurality of majority data subsets and minority data sets.

According to an embodiment, the method includes allocating, with a weighing module, each of the plurality of classifiers with an equal weightage, to obtain the plurality of weighted classifiers.

According to an embodiment, the method includes building the classification model with a support vector machine.

According to an embodiment, the method includes: receiving, with an over-sampling module, the first majority data subset and the first minority data set from the sampling module; and creating a first synthetic data set by applying a process of synthetic over-sampling with replacement on the first majority data subset and the first minority data set.

According to an embodiment, the method includes over-sampling the first minority data set by taking a data point in the first minority data set and introducing synthetic examples along a line segment joining the data point to a predetermined number of data point neighbors.

According to an embodiment, the method includes: building a first classification model with a training module based on the first majority data subset and the first minority data set corresponding to the first classifier; validating the first classification model against the first synthetic data set with a validation module; and obtaining a resultant prediction accuracy of the first classification model, representing the importance of the first classifier.

According to an embodiment, the method includes: receiving, with the over-sampling module, a plurality of majority data subsets and minority data sets from the sampling module; and creating, with the over-sampling module, a plurality of synthetic data sets; building, with the training module, a plurality of classification models representing a plurality of classifiers with the received plurality of majority data subsets and minority data sets; validating, with the validation module, the plurality of classification models against the plurality of synthetic data sets, and obtains a plurality of prediction accuracies of the classification models, representing the importance of each of the plurality of classifiers.

According to an embodiment, the method includes allocating, with a weighing module, each of the plurality of classifiers with a weightage according to its importance, to obtain the plurality of weighted classifiers.

According to an embodiment, the method includes: receiving, with a testing module, any of the first input parameter, the at least one HRV parameter, and the at least one ECG parameter; evaluating the parameter with its corresponding weighted classifier; and generating a binary prediction output of either 0 or 1 for each evaluated weighted classifier.

According to an embodiment, the method includes calculating, with a scoring module, the risk score based on a normalized summation of the binary prediction outputs of all evaluated weighted classifiers.

According to a third aspect of the present disclosure, there is provided a method of determining a risk score, including: receiving a first imbalanced dataset corresponding to a first classifier and sampling the data samples to form a first balanced data set; creating a first synthetic data set by applying a process of synthetic over-sampling with replacement on the first balanced data set; building a first classification model based on the first balanced data set corresponding to the first classifier; validating the first classification model against the first synthetic data set; and obtaining a resultant prediction accuracy of the first classification model, representing the importance of the first classifier.

According to an embodiment, the method includes: obtaining a plurality of prediction accuracies relating to a plurality of classification models; sorting the plurality of classification models according to its prediction accuracy; allocating each of the plurality of classification models with a weightage according to its importance to obtain a plurality of weighted classifiers; evaluating an input parameter with its corresponding weighted classifier; and generating a binary prediction output of either 0 or 1 for each evaluated weighted classifier; and calculating the risk score based on a normalized summation of the binary prediction outputs of all evaluated weighted classifiers.

According to a fourth aspect of the present disclosure, there is provided a system for determining a cardiac event risk score, including: an ensemble-based scoring system, configured to receive any one of (a) a vital signs parameter, (b) an ECG parameter extracted from an ECG established by carrying out an ECG procedure, and (c) a HRV parameter determined from a HRV analysis of the ECG, the ensemble-based scoring system including: a plurality of weighted classifiers for providing a risk score calculation, the plurality of weighted classifiers established based on past patient data in a database of accumulated past patient data; and an analysis module for receiving the at least one HRV parameter, and the at least one ECG parameter transmitted to the ensemble-based scoring system, wherein the analysis module determines a cardiac event risk score by comparing any one of the vital signs parameter, the at least one HRV parameter, and the at least one ECG parameter, to corresponding weighted classifiers.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" herein means "and/or" unless specifically indicated otherwise.

As used herein, the term "set" corresponds to or is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, a structural feature, an object, a process, a physical parameter, or a value depending upon the type of set under consideration.

The terms "group" and "gang" as used herein correspond to or are defined as an organization of two or more elements, e.g., a group or gang can be defined as a set having at least two components. The term "subgroup" as used herein corresponds to or is defined as a portion of a group or gang, and hence corresponds to or can be defined as an organization of at least one element, e.g., a subgroup can be defined as a set having at least one component.

Triage Systems

In a present embodiment of the disclosure, there is provided a system for determining a risk score for a hospital emergency department triage, in particular triage for acute coronary syndromes (ACS) which include any group of symptoms attributed to the obstruction of the coronary arteries. An embodiment of the disclosure can also determine a risk score in an environment other than a hospital emergency department triage, for instance, in an ambulance, clinic, ward, intensive care unit (ICU), and home or non-medical workplace environment.

Patients presenting to the ED of a hospital with chest pain have varying levels of risk of complications in the acute phase of treatment (<72 hours). With regard to a hospital ED having limited resources, especially doctors and specialists, it is desired, and in fact necessary for the incoming patient to undergo risk stratification with a triage process to efficiently address the patient's situation as well as for efficient allocation of resources.

Present scoring systems, as mentioned, do not effectively provide insight and risk assessment, especially in the area of ACS. The thrombolysis in myocardial infarction (TIMI) risk assessment is currently the most clinically accepted risk categorization of patients complaining of ACS. However, the prediction accuracy is being put to question by part of the scientific community, for example, in Hess, et al's paper on "Prospective validation of a modified thrombolysis in myocardial infarction risk score in emergency department patients with chest pain and possible acute coronary syndrome". In this paper, Hess et al. identified that "a modified TIMI score assessment outperformed the original with regard to diagnostic accuracy . . . . However, both scores are insufficiently sensitive and specific to recommend as the sole means of determining disposition in ED chest pain patients".

Electrocardiography is a non-invasive procedure used by medical professionals to obtain a measure of the electrical activity of a patient's heart, and is carried out by attaching electrodes to the outer surface of a patient's body, and processed by an external processing system. The resultant interpretation of the electrical signals is termed as an electrocardiogram (ECG) and is able to provide insight into any abnormal functionality or rhythms of the patient's heart.

Detection of the heart's electrical activity is provided by attached electrodes. In general, the more electrodes are attached, the more information that may be obtained from the resultant readings. Particular configurations of electrodes have been established in terms of "leads", where a lead refers to the tracing of voltage difference between two electrodes. Typically, configurations are provided for 3, 5, or 12 lead ECGs, where 3 electrodes are used to obtain a 3-lead ECG, 5 electrodes are used to obtain a 5-lead ECG, and 10 electrodes are used to obtain a 12-lead ECG.

FIG. 1 illustrates a patient 10 connected to the ten electrodes 12 needed for a 12-lead ECG 14. Multiple electrodes are required at various locations on a patient's chest, as well as electrodes on each of the limbs of the patient. The 12-lead ECGs are tools that may be found frequently in hospitals, typically in Intensive Care Units or High-dependency monitoring beds, as the output of a 12-lead ECG provides a more detailed look at three areas of the patient's heart—the anterior, lateral and inferior, and changes in certain segments of the ECG may suggest an area of concern. However, the 12-lead ECG requires trained personnel to accurately administer the 10 electrodes. Further, in order to extract the more pertinent information from the 12-lead ECG, experienced and highly trained clinicians are required for interpretation.

The above difficulties limit the usage of the 12-lead ECG as a triage tool in the ED. Prompt attention and assessment is usually required for incoming patients complaining of chest pain, and there typically may not be availability of specially trained nurses and doctors to both administer the electrodes as well as to interpret the results. 12-lead ECGs are intended for an in-depth "snapshot" view of a patient's cardiac situation. Unfortunately, in the ED, such elaborate in-depth view may not subject to a prompt interpretation, and as such, 3-lead ECGs are much more typically found in the EDs.

The applicants of the present invention had also previously developed machine learning based risk assessment tools for identifying cardiac risk in patients presenting to the ED, and incorporate by reference the specifications identified as patent publication WO2011/115576.

Discussion of Prior Art Documents

In the present embodiment, it is envisioned that a quick and accurate triage tool be provided for use to assess presented patients complaining of chest pain, and operated by clinicians who can be presented with a risk score as assessment, and do not have to be highly experienced or highly trained specialists.

System Architecture of Triage System of the Present Embodiment

Figure 2:
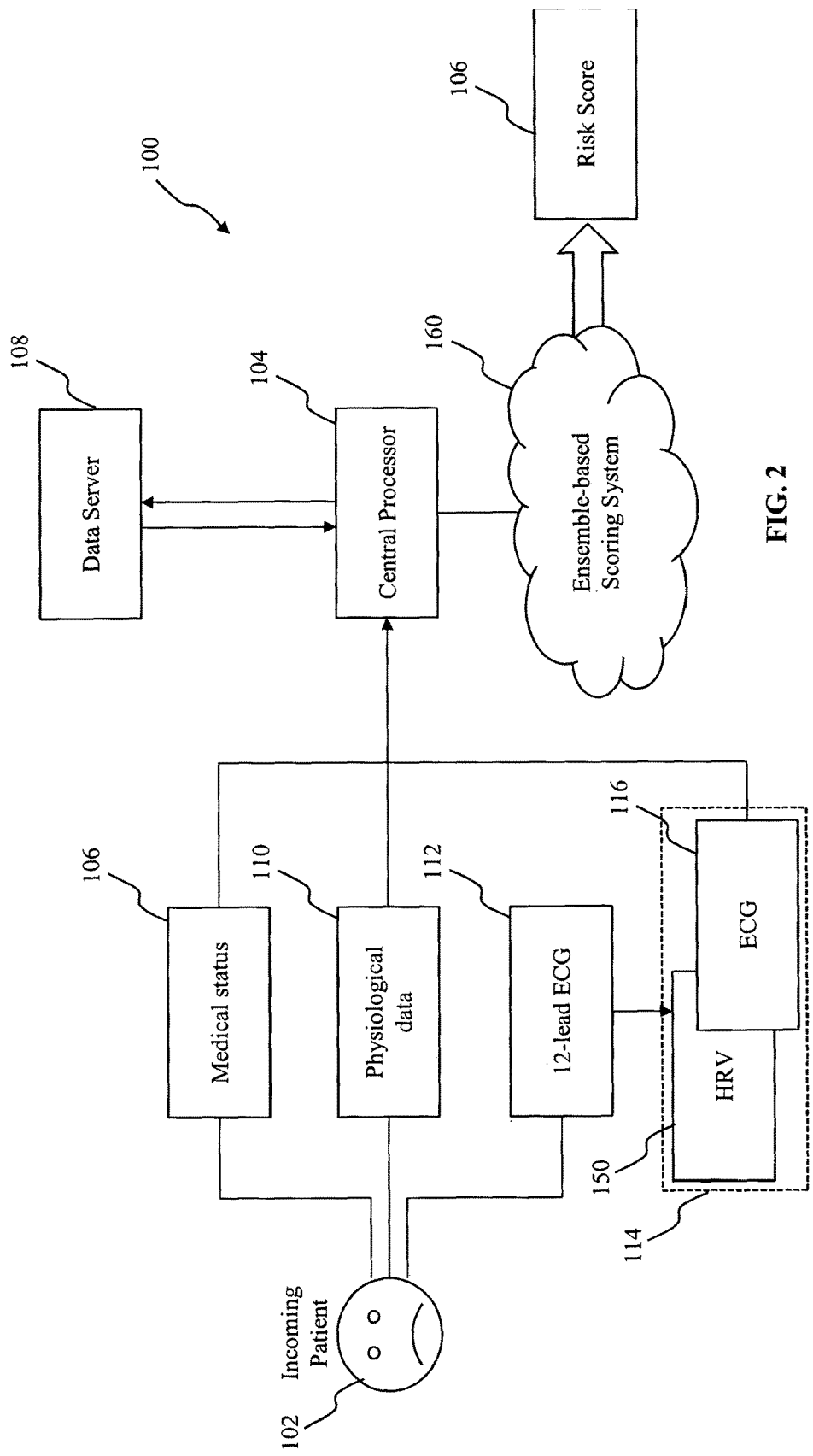
FIG. 2 illustrates a system architecture of a triage system of the present embodiment.

FIG. 2 illustrates a system architecture of a triage system of the present embodiment. Triage system 100 is provided, which is designed to be applied onto an incoming patient 102 presented to the ED and complaining of chest pains. The triage system 100 is intended to be a clinical tool for use in the ED, to assess incoming patients, and to provide a risk score as an output. The risk score in such a system pertains to risk stratification of ACS in the patient, where perhaps a low score indicates that the chest pain is self-limited, while a high score indicates the imminent possibility of cardiac arrest and/or lethal arrhythmias.

As an overview, the triage system 100 utilizes physiological and cardiac data measurements, compiled with medical status information, and processes such inputs within an intelligent machine-learning scoring system which compares the present input to correlated past patient diagnoses, in order to provide an insightful risk score as to the risk of ACS in the patient.

In the present embodiment, at least one medical status input 106 pertaining to the incoming patient 102 is provided to the triage system 100. In the embodiment, a computer interface system provided for an ED nurse to register the incoming patent 102, and to enter pertinent information relating to the medical status input 106 of the patient 102. The medical status input 106 is thereafter transmitted and logged into a triage system central processor 104, under an identifier for the patient, typically by name or by identity registration number.

The medical status input 106 may be a medical history of the patient, a drug history, a drug allergy, a smoking history, a family history of ischemic heart disease, a record of angina events in the past 24 hours, an indication or description of current ailment or any other information or factor which may be useful in the assessment or determination of whether the patient may suffer or may already be suffering from ACS. It can also include patient age, gender and demographic information.

Such medical status input 106 is typically taken through an oral interview with the patient, but should a patient be somehow incapable of regular conversation or does not have access to such pertinent information or be incapacitated in any way, it is envisioned that the central processor, is able to communicate with a centralized data server 108 which has stored in memory such medical status input 106 of the patient 102. The central processor 104 is thus capable of accessing the data server 108, polling the data server 108 based on the relevant patient identifier, retrieving the information required, and propagating the information into the present triage assessment. In the present embodiment, the centralized data server 108 is a hospital data server providing and collecting information through various workstations in the hospital, and where the patient 102 has on previous occasion visited the hospital and provided information pertaining to his medical status and history. Alternatively, the centralized data server 108 may be a regional or national data server, where hospitals and medical care facilities share patient information, subject of course to relevant privacy laws and guidelines.

Physiological Measurements

The triage system 100 of the present embodiment also seeks to obtain as physiological data input 110 from the patient 102 in the assessment of risk. Physiological data in the present case, may refer to a vital sign data of the patient 102. Vital sign data may be defined as clinical measurements that indicate the state of a patient's essential body functions. For example, vital sign data may refer to a heart rate, a respiratory rate, a blood pressure reading, a temperature reading, a Glasgow Coma Score (GCS), an saturation of peripheral oxygen ($SpO_2$) reading, a pain score, or any other measurement or reading obtained from the patient which may be relevant in the assessment of ACS.

To obtain such physiological data 110, the above vital signs may be measured as follows. For example, the heart rate and the systolic and diastolic components of a blood pressure reading may be measured using a combination blood pressure measurement device such as the Propaq CS Vital Signs Monitor. Alternatively, devices such as a sphygmomanometer or a mercury manometer may be used to measure blood pressure. Heart rate, oxygen saturation reading and respiratory rate may be measured using a pneumogram. Separately, heart rate may be monitored with a simple pulse monitor, and oxygen saturation may be measured with a pulse oximeter. Measurement of $SpO_2$ may also be known as pulse oximetry, and as defined is the ratio of oxyhemoglobin to the total concentration of hemoglobin present in the blood.

Glasgow coma scale (GCS) refers to the degree of spontaneity of the patient's physical (such as limbs, eyes) motor and/or verbal response to instructions from a medical professional. Pain score refers to the degree of response (such as adduction, pronation or extension of a limb or body part; flexion or withdrawal) to pain applied to the patient. Tympanic (ear) temperature may be recorded using a tympanic thermometer.

Further, AVPU ("alert, voice, pain, unresponsive") scores are recorded at triage and scored according to the best response during the collection. A modified early warning score (MEWS) is also calculated based on collected data during presentation to the ED. MEWS provides a simple guide to determine illness of a patient, and is based on the four physiological readings (systolic blood pressure, heart rate, respiratory rate, body temperature) and one observation (level of consciousness, AVPU).

Further, in the present embodiment, the presenting patient is also put through an immunoassay test to measure the presence of cardiac-Troponin T serum levels, which may infer cardiac conditions such as myocardial infarction.

In the embodiment, the central processor 104 includes sufficient signal acquisition and processing capabilities to receive directly the signal input from any or all of the physiological data inputs 110. Alternatively, the triage system 100 consolidates the measurement and obtaining of the above physiological inputs 110 in a self-contained physiological data processing unit and thereafter provides digital signals to the central processor 104 for sorting and further processing.

Also, the central processor 104 may similarly access a centralized data server to obtain records of previously measured physiological data 110, and carry out a comparison with respect to present readings, to chart any differences in the patient's physiological state, and perhaps provide an additional insight for a risk assessment.

12-lead ECG—Setup

In the present embodiment, a 12-lead ECG procedure is carried out by a 12-lead ECG machine 112 or an ECG sensor to provide understanding as to the electrical activity and function of the patient's 102 heart. In the embodiment, a Philips PageWriter TC series device is used. In order to carry out the procedure, the attending ED nurse has to accurately attach the ten electrodes required (refer to FIG. 1 for specific locations) in order to adequately obtain electrical activity readings of the patient's heart, which are thereafter interpreted into an ECG. Typically, ECGs are provided as a continuous printout of the electrical signals as detected by the attached electrodes. In the embodiment, a 5 minute ECG reading is used in the triage, but any other time period which allows for relevant readings to be obtained may be similarly used.

In the present embodiment, the resultant ECG signals are provided to an ECG post-processing module 114 provided as an application program on a memory module for operation on a processor on the 12-lead ECG machine 112, the ECG post-processing module including a data acquisition device (DAQ) for receiving the analog sensor inputs. Sampling of the ECG sensors is carried out at 125 Hz. In the embodiment, the post-processing module 114 utilizes a LABVIEW interface embedded with MATLAB code for data processing of the acquired electrical signals from the attached electrodes. The ECG is converted into a digital signal format to allow easy manipulation and interpretation of the acquired electrode signal readings. With regard to the term "module", it is stated that the term refers to the particular function or functions performed by the associated processing unit; the "module" may or may not correspond to actual electrical circuitry.

The ECG post-processing module also operates a filter module (not shown) which processes the raw ECG data from the 12-lead ECG machine 112 to suppress unwanted signals such as noise, motion, motion artifacts, power line interference, and carries out any other manipulation necessary for the accurate observation and interpretation of the ECG 120. A 5-28 Hz band-pass filter is used in the present embodiment, but other suitable configurations may also be possible.

Alternatively, the ECG signals obtained by the 12-lead ECG machine 112 are directly provided to the central processor 104 and processed by an ECG post processing module operating on the central processor 104.

In the present embodiment, an ECG extraction module 116 is provided for operation within the framework of the ECG post-processing model 114. The ECG extraction module 116 is configured to act upon the digitized stream of electrical signal activity as obtained by the 12-lead ECG machine 112. In addition, the ECG extraction module 116 acts upon the filtered digitized stream of electrical signal activity as obtained by the 12-lead ECG machine 112.

In the embodiment, the 12-lead ECG machine 112 also generates a continuous hardcopy paper printout of the resultant ECG signals such that a trained medical practitioner may further analyze or cross-compare results of the ECG with a risk score provided by the present triage system 100. The printout function could also be provided upon request by the central processor 104, instead of a continuous hardcopy printout.

ECG—Interpretation

FIG. 3A illustrates a sample ECG printout 120 as provided by the triage system of the present embodiment. ECG 120 is a cutout of a continuous monitoring that provides a snapshot view of the electrical activity signal monitoring of a patient 102 as hooked onto the triage system 100.

A trove of information can be gleaned from the ECG 120 as to the health and condition of a human heart. As mentioned above, not all medical personnel working in the ED of a hospital are trained for such ECG interpretation and analysis. The triage system 100 of the present disclosure provides an ECG extraction module 116 which analyzes the ECG 120 and extracts parameters which provide such cardiac status insight.

The ECG 120 sets out the 12 leads or voltage difference measurements between 2 electrodes. Essentially, the electrical activity of the following leads are monitored and displayed as requested on the ECG 120: I, II, III, aVR, aVL, aVF, V1, V2, V3, V4, V5, V6. In this embodiment, the 12 leads are combined on to 3 concurrent trace lines. Alternatively, the 12 leads could be provided onto 12 separate trace lines.

Within an ECG tracing of the heartbeat, or the cardiac cycle, there is provided a P wave, a QRS complex, a T wave, and a U wave. The baseline voltage 121 of the electrocardiogram is known as the isoelectric line. Typically, the isoelectric line or the baseline voltage 121 is measured as the portion of the tracing following the T wave and preceding the next P wave. FIG. 3B illustrates a close up of the cardiac cycle 122 from the ECG 120.

In medical definitions, the P wave 124 describes the main electrical vector directed from the sinoatrial node (SA node) towards the atrioventricular node (AV node), and spreads from the right atrium to the left atrium. The QRS complex 126 represents a depolarization of the left and right ventricles leading to a contraction of the heart. The ventricles have a larger muscle mass as compared to the atria, so the QRS complex 126 usually has a much larger amplitude than the P-wave.

In the present embodiment, a modified threshold-plus-derivative method was used to detect the QRS complexes, and all ectopics and other non-sinus beats were excluded in accordance with the guidelines outlined by the Task Force of the European Society of Cardiology and the North American Society of Pacing and Electrophysiology.

FIG. 3C illustrates a close up of the QRS complex 126 of the cardiac cycle of FIG. 3B. The Q wave 128 is an initial negative deflection in the QRS complex 126, and may or may not be present in a patient's ECG readings. An abnormality in the Q wave 128 may indicate the presence of an infarction in the patient 102. RR intervals were then calculated based on the sinus rhythm.

The R wave 130 is the initial upward deflection of the QRS complex 126, following the Q wave 128 in the ECG 120 and representing an early depolarization of the ventricles. The maximum amplitude of the R wave 130 is referred to as the R peak amplitude, and is established by the amplitude of the R wave deflection as measured from the baseline, or the isoelectric line. A poor R wave progression may be attributed to anterior myocardial infarction, or could also be caused by left bundle branch block, or Wolff-Parkinson-White syndrome, or right and left ventricular hypertrophy.

An RR interval 136 can be extracted from the ECG 120, which may be defined as the interval between an R wave 130 and a subsequent R wave on the ECG. The RR interval 138 is ECG-extracted interpretation of the patient's heart rate.

S wave 132 is defined as the downward deflection of the QRS complex 126 following the R wave in the ECG and represents a late depolarization of the ventricles. Also determinable from the QRS complex 126 is the QRS duration 134 which is defined as time period between the initial deflection of the Q wave 128 and the end of the S wave 132 deflection. A prolonged QRS duration 134 may indicate a hyperkalemia or a bundle branch block.

A QRS amplitude can also be obtained from the QRS complex 126, where the amplitudes of the negative Q wave 128 and S wave 132 are subtracted from the amplitude of the positive R wave 130. An increased amplitude may indicate cardiac hypertrophy. The ventricular activation time (VAT) 138, defined as the time duration between the beginning or the initial deflection point of the Q wave 128 and the peak of the R wave 130, could be an indication of diastolic dysfunction.

A QRS axis can also be determined from the QRS complex 126, where the QRS axis is the averaged direction of electrical activity during ventricular depolarization, or the net vector of ventricular depolarization. It can also be defined as the direction in which the mean QRS current flows. The ECG extraction module 116 is able to process and indicate whether the QRS axis is in normal or in deviation towards the left or the right, which should be sufficient for clinical interpretation. Specific angle calculation could also be possible, if necessary.

Returning to FIG. 3B, T wave 140 occurs after the QRS complex 126 and represents the repolarization (or recovery) of the ventricles. The interval from the beginning of the QRS complex 126 to the apex of the T wave 140 is referred to as the absolute refractory period. The last half of the T wave 140 is referred to as the relative refractory period (or vulnerable period). The T wave 140 can be described by its symmetry, skewness, slope of ascending and descending limbs, amplitude and subintervals like the $T_{peak}-T_{end}$ interval. T wave inversion, or negative T waves, may be a sign of coronary ischemia, Wellens' syndrome, left ventricular hypertrophy, or central nervous system disorder.

The QT interval 142 is measured from the beginning of the QRS complex 126, i.e. the initial negative deflection of the Q wave 128, to the end of the T wave 140. A prolonged QT interval 142 is a risk factor for ventricular tachyarrhythmias and sudden death. The QT interval 142 varies with heart rate—the faster the heart rate, the shorter the QT interval, and for clinical relevance requires a correction for this, giving the QT interval correction (QTc). In the present embodiment, Bazett's formula is used in the calculation of the QTc, but other methodologies may also be used. Bazett's formula is provided as follows:

$$QT_C = \frac{QT}{\sqrt{RR}} \quad (1)$$

The ST segment 144 represents the connection between the QRS complex 126 and the T wave 140. The ST segment 144 represents the period when the ventricles are depolarized. Typically, the ST segment 144 is isoelectric and matched with the baseline. An ST elevation may be defined when the ST segment 144 is abnormally high above the isolectric baseline 121. The ST elevation is obtained by measuring the vertical elevation between the ECG trace of the ST segment 144 and the baseline 121, and may correspond to damage or pathlogical change to the cardiac muscle.

Presence of a left bundle branch block (LBBB), a cardiac conduction abnormality, is assessed for in the present embodiment. In a LBBB, activation of the left ventricle is delayed, which causes the left ventricle to contract later than the right ventricle. Criteria to observe or assess a LBBB would include any or all of the following: The heart rhythm must be supraventricular in origin; the QRS duration must be ≥120 ms; there should be a QS or rS complex in lead V1, there should be a RsR' wave in lead V6; the T wave 140 should be deflected opposite the terminal deflection of the QRS complex 126. Some of the causes of LBBB could be aortic stenosis, dilated cardiomyopathy, acute myocardial infarction, or extensive coronary artery disease.

A right bundle branch block (RBBB) is also assessed, where in a RBBB, the right ventricle is not directly activated by impulses travelling through the right bundle branch. Criteria to observe or assess a RBBB would include any or all of the following: The heart rhythm must originate above the ventricles (i.e. SA, atria or AN) to activate the conduction system at the correct point; the QRS duration must be more than 100 ms (incomplete block) or more than 120 ms (complete block); there should be a terminal R wave in lead V1 (e.g. R, rR', rsR', rSR' or qR); there should be a slurred S wave in leads I and V6; the T wave 140 should be deflected opposite the terminal deflection of the QRS complex 126. An atrial septal defect is one possible cause of a RBBB.

In the embodiment, ECG extraction module 116 seeks to characterize an intraventricular conduction delay (IVCD). IVCD could be determined from a QRS duration 134 widening, where by a process of elimination, the QRS duration widening is caused by an IVCD if the manifestation is not caused by a LBBB or a RBBB. IVCD may correspond to a myocardial infarction, a cardiomyopathy with ventricular fibrosis, or a chamber enlargement.

Atrial abnormalities or atrial enlargements, atrial dilatations or atrial hypertrophy may also be detected in an ECG. Typically, such abnormalities are found on the P wave 124, and in leads II, III, aVF or V1. In sinus rhythm, a right atrial depolarization wave precedes that of the left atrium and the combined depolarization wave is the P wave 124.

In a right atrial abnormality, the right atrial depolarization lasts longer than normal and its wave extends to into the left atrial depolarization. Although the amplitude of the right atrial depolarization current remains unchanged, its peak now falls on top of that of the left atrial depolarization wave. As a result, the combined the P wave, is taller than normal but its width remains.

In a left atrial abnormality, the left atrial depolarization lasts longer than normal but its amplitude remains unchanged. Therefore, the height of the resultant P wave remains within normal limits but its duration is extended. A notch (broken line) near its peak may or may not be present. More quantitative analysis may also be provided to obtain a left atrial abnormality and a right atrial abnormality.

Ventricular hypertrophy (VH) is the thickening of the ventricular walls (lower chambers) in the heart. Although left ventricular hypertrophy (LVH) is more common, enlargement can also occur in the right ventricle, or both ventricles. While ventricular hypertrophy occurs naturally as a reaction to aerobic exercise and strength training, it is most frequently referred to as a pathological reaction to cardiovascular disease, or high blood pressure.

In the embodiment, the Sokolow-Lyon index is used to diagnose LVH in the ECG, although the accuracy of diagnoses is increased with the use of multiple criteria sets. In Sokolow-Lyon, the criteria for diagnosis is for S in V1+R in V5 or V6 (whichever is larger) ≥35 mm; and R in aVL≥11 mm. Causes of increased afterload that can cause LVH include aortic stenosis, aortic insufficiency and hypertension. Primary disease of the muscle of the heart that cause LVH are known as hypertrophic cardiomyopathies, which can lead into heart failure. Long-standing mitral insufficiency also leads to LVH as a compensatory mechanism.

In right ventricular hypertrophy, (RVH), conditions occur which decrease pulmonary circulation, meaning blood does not flow well from the heart to the lungs, and extra stress can be placed on the right ventricle. An ECG with right ventricular hypertrophy may or may not show a right axis deviation on the ECG. Certain criteria for assessment may include any one or more of the following: right axis deviation (>90 degrees) in presence of disease capable of causing RVH; R in aVR>5 mm; R in aVR>Q in aVR; any one of the following in lead V1: R/S ratio>1 and negative T wave; qR pattern; R>6 mm, or S<2 mm, or rSR' with R'>10 mm.

Atrial fibrillation (AF) is the most common cardiac arrhythmia (irregular heart beat). In AF, the normal regular electrical impulses generated by the sinoatrial node are overwhelmed by disorganized electrical impulses usually originating in the roots of the pulmonary veins, leading to irregular conduction of impulses to the ventricles which generate the heartbeat. AF may occur in episodes lasting from minutes to days ("paroxysmal"), or be permanent in nature. A number of medical conditions increase the risk of AF, particularly mitral stenosis (narrowing of the mitral valve of the heart).

In the diagnosis of AF, characteristic would be the absence of P waves, with disorganized electrical activity in their place, and irregular R-R intervals due to irregular conduction of impulses to the ventricles.

Other characteristics or parameters which can aid with the diagnosis or assessment of a risk score as to determining ACS for a patient can also be extracted from the 12-lead ECG and provided for analysis.

HRV

In the embodiment, a heart rate variability (HRV) extraction module 150 is provided in the ECG post-processing module 114 and functions to extract parameters related to HRV from the ECG 120.

As mentioned above, several systems and methodologies seek to provide such input for risk stratification utilizing a plurality of parameters for such determination. In addition to the various clinical factors as presented above, HRV is a potentially useful approach that can be applied at the point of clinical assessment.

HRV is the physiological phenomenon of variation in the time interval between heartbeats and is defined as variation in the beat-to-beat interval. HRV is sometimes also known as RR interval 136 variability. The R-wave of a particular heartbeat corresponds to the point in the cardiac cycle of the early systolic phase, and from a signal processing point of view, provides a reliable time-fiducial for making cardiac cycle interval measurements.

Variation in the beat-to-beat interval is a physiological phenomenon. The SA node of the heart receives several different inputs and the instantaneous heart rate or RR interval and its variation are the results of these inputs. HRV is affected by the autonomic nervous system, which consists of the sympathetic nervous system (SNS) and the parasympathetic nervous system (PSNS), and which are also inputs to the SA node.

Observed HRV is believed to be an indicator of the dynamic interaction and balance between the SNS and PNS, providing a measure of nervous system competence. HRV serves as an indicator for the diagnosis and assessment of a variety of conditions that are affected by the autonomic system ranging from congestive heart failure to sleep apnoea. For example, reduced HRV is sometimes believed to be an independent predictor of cardiac death and mortality after myocardial infarction in patients. Reduced HRV is also seen after sudden cardiac arrest and in patients with diseases such as diabetes, uraemia and hypertension.

HRV Parameters

From detected QRS complexes 126 in the ECG 120, the processed RR intervals 136 can be obtained. The RR intervals 136 are used to calculate the following HRV parameters, from which include time domain and frequency domain analyses.

Examples of Time Domain Measures are:

Time Domain Measures

1. Average length of the RR interval (aRR): Mean of all sinus RR intervals (N-N) in sequence
2. Standard deviation of all N-N interval (SDNN)
3. Mean heart rate (mean HR)
4. Standard deviation of all instantaneous heart rate values (SDHR)
5. NN50 (count): Number of consecutive RR intervals differing by more than 50 ms
6. pNN50(%): Percentage of consecutive RR intervals differing by more than 50 ms
7. HRV triangular index: Total number of all N-N intervals divided by the height of the histogram of all NN intervals.
8. Baseline width of a triangle fit into the N-N interval histogram using a least squares technique (TINN)
9. Square root of the mean squared differences of successive N-N intervals (RMSSD): The square root of the mean of the sum of the squares of differences between adjacent N-N intervals.

Frequency Domain Measures

Frequency domain measures are calculated based on the power spectrum of the RRI sequence which is generated using a Lomb-Scargle periodogram. The following parameters are then calculated:

1. Total power (TP) ($ms^2$): Variance of N-N intervals over the segment till 0.4 Hz
2. VLF ($ms^2$): Power in very low frequency range (<0.04 Hz)
3. LF ($ms^2$): Power in low frequency range (0.04-0.15 Hz)
4. HF ($ms^2$): Power in high frequency range. (0.15-0.4 Hz)
5. LF norm (nu): LF power in normalized units: LF norm=LF/(TP−VLF)×100%
6. HF norm (nu): HF power in normalized units: HF norm=HF/(TP−VLF)×100%
7. LF/HF: Ratio of LF/HF The extracted parameters are thereafter provided to the central processing unit 104 for further processing.

In summary, the triage system 100 utilizes the above information and parameters obtained through medical status input 106, the physiological data input 110, the 12-lead ECG machine 112 and subsequently the ECG extraction module 116 and the HRV extraction module 150, to determine relevant weighted classifiers, which relate to the importance of the information and/or parameter to the determination of ACS.

Previous Patient Data Collection

Further provided in the triage system 100 of the present embodiment, is an access to a database of accumulated past patient data. Such a database is hosted on a centralized data server 108, for which the central processor 104 of the triage system 100 has data access to. An ensemble-based scoring system 160 is provided and operates on the central processor 104 which utilizes the accumulated past patient data in training up a machine learning structure, on which reliable decisions can be expected.

In the present disclosure, past patient data is collated from patients presented to the ED of a hospital with undifferentiated and non-traumatic chest pain. Patients in non-sinus rhythm (e.g. asystole, supraventricular and ventricular arrhythmias, complete heart block) and patients who were discharged against medical advice or transferred to another hospital within 72 hours of arrival at the ED were excluded. An eligible patient who arrived at the ED with chest pain was randomly screened and recruited by trained medical personnel.

The outcome of the study was a compilation of severe complications within 72 hours of arrival at the ED, extracted from the electronic hospital records. Patients were considered to have met the outcome if they had at least one of the following severe complications: all-cause mortality, cardiac arrest, sustained ventricular tachycardia (VT), hypotension requiring inotropes or intra-aortic balloon pump (IABP) insertion, intubation or mechanical ventilation, complete heart block, and bradycardia requiring insertion of a pacing wire.

Parameters of data which are recorded and extracted by the present triage system 100 include any or all of the parameters listed above, as well as any other not listed, but which may assist in the assessment of ACS. Further, the outcomes of the past patients from the visit to the ED are also utilized, which provides the reference for the various data parameters.

With the advancement of computational techniques, machine learning has been found to be useful for scoring systems to improve predictive performance, handle imbalanced data and enhance system adaptability. In the present disclosure, the ensemble-based scoring system 160 is provided where an intention is to provide an intelligent scoring system in combining HRV and 12-lead ECG parameters and vital signs to predict acute cardiac complications within 72 hours among critically ill patients presented with chest pain. The scoring system 160 of the present embodiment utilizes a unique machine learning structure, with which reliable decisions can be expected.

Upon collating of past patient data, and investigating such data, it was found that the outcome distribution is highly imbalanced. Imbalanced data is defined where there exists a majority class with normal data and a minority class with abnormal data, in this case, patients with acute cardiac complications within 72 hours. When applying machine learning algorithms on such an imbalanced dataset, the majority class will dominate the learning process and consequently results in poor generalization performance on unknown testing samples. Typical solutions to handle imbalanced data include under-sampling majority classes and over-sampling minority classes. However, the prevalence rate observed from the resultant pilot data is fairly low (<5%). As a result, neither state-of-the-art classification techniques nor conventional imbalance handling strategies may be able to provide satisfactory prediction results. In order to provide reliable prognosis with HRV parameters, 12-lead ECG parameters and vital signs, a learning framework tailored specifically for imbalanced data is important and will serve as a major factor in controlling system performance.

The applicants have previously proposed a geometric distance based scoring system in which inputs were continuous variables, which may be applicable to parameters such as heart rate, blood pressure, or respiratory rate amongst others under physiological data inputs and even HRV parameters as extracted from the ECG. In the present disclosure, it is intended for 12-lead ECG parameters to be integrated into the scoring model; however, these measurements are in discrete format, i.e., either 0 or 1. As a result, a new scoring system is required, which is able to handle both continuous and discrete variables as inputs.

Prior to calculation of the machine learning score, the original inputs should be classified into a [−1, 1] interval by performing a min-max normalization. Given a dataset $X=[x_1, x_2, \ldots, x_K]$ where each x represents a patient, $min_A$ and $max_A$ are then defined to denote the minimum and maximum values of an attribute vector $A=[x_1(m), \ldots, x_K(m)]$, where m is the number of features (in the embodiment, m is the total number of 12-lead ECG parameters, HRV parameters and vital signs being utilized as classifiers) and K is the total number of past patient data samples. Min-max normalization maps a value, v, of A to v in the range $[min_A, maxA_A]$ by computing the equation:

$$v' = \frac{v - min_A}{max_A - min_A}(max'_A - min'_A) + min'_A \quad (2)$$

It is noted that the normalization process is able to preserve the relationships among the original data values, which therefore facilitates the machine learning based risk score prediction in the ensemble-based scoring system 160.

Ensemble-Based Decision Making

In the medical community, it is good practice for medical practitioners to seek a second or further opinion before making a final decision on the situation. By consulting several experts with various backgrounds, medical practitioners can weigh their suggestions or pick up the most informed one. For example, the suggestion by a senior clinician could be given a higher weight than that of a junior clinician. In critically ill cases, final decisions may be given by a committee of experts in a discussion and outcome even put to a vote. Given a desire to operate as closely as possible to real-world situations, computational intelligence methods seek to simulate the process of decision from multiple experts. Such intelligent learning systems have various names such as ensemble learning systems, mixture of experts, and multiple classifier systems.

Figure 4A:
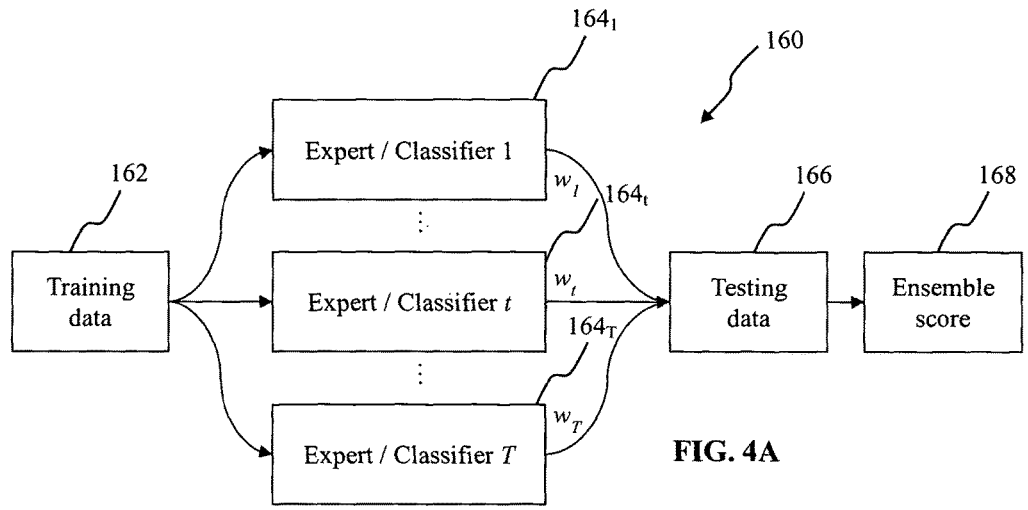
FIG. 4A illustrates a general structure of ensemble learning based system.

The principle behind these techniques is to discover an optimal way to combine the suggestions of individual experts so as to achieve a reliable final decision. FIG. 4A illustrates a general structure of ensemble learning based system. Within this structure, each individual expert may be referred to as a classifier 164. In FIG. 4A, classifier 164$_1$ references classifier 1, classifier 164$_t$ references classifier t, and classifier 164$_T$ references classifier T. Similar features of similar functions are similarly numbered. In the present embodiment, each expert also refers to a parameter which may provide an insight to the assessment of ACS in a patient. Each ensemble classifier is provided a weight to represent the importance of that classifier. In the present disclosure, the weight is determined by the contribution of its corresponding classifier and is derived from training process, i.e. the weightage of the classifier is related to the relevance of that particular parameter in the assessment of ACS.

Typical ensemble learning methods usually generate a predictive label rather than a score as the output. However, and as mentioned previously, a risk score is more informative than a class label to clinicians in providing insight for decision making. In the present disclosure, a simple ensemble score or risk score 168 is provided as the prediction output of the system.

In the embodiment, access is from the triage system 100 and the ensemble-based scoring system 160 to a training dataset 162. Training dataset 162 is also referenced by L and includes K samples $(x_k, y_k)$ where k=1, 2, ..., K and $y_k$ is the class label. Given an incoming testing sample x from testing data 166 obtained from the central processor 104 of the triage system 100 as applied to an incoming patient, its label y can be predicted by a single classifier $\varphi(x, L)$ where the class label is either $C_0$ or $C_1$. In the present disclosure, label $C_0$ indicates that the patient is normal (a negative ACS outcome) while label $C_1$ indicates that the patient has acute cardiac complications within 72 hours (a positive ACS outcome). As illustrated in FIG. 4A, a set of T independent classifiers can be derived from input parameters, and their corresponding weights can be determined from a sample training data set 162. The risk score 168 on sample x is calculated using the equation as follows:

$$RS_x = \frac{\sum_{y \in C_1} \varphi_t(x, L) \cdot w_t}{\sum_{y \in C_1} \varphi_t(x, L) \cdot w_t + \sum_{y \in C_0} (1 - \varphi_t(x, L)) \cdot w_t} \times 100 \quad (3)$$

where the output of classifier $\varphi_t(x, L)$ is either 0 or 1 and its corresponding predicted label y is $C_0$ or $C_1$, respectively.

The risk score is based on the measurements of weighted positive prediction and weighted negative prediction. The weighted positive prediction is defined as the sum of weights whose corresponding classifiers predict a label of $C_1$ while the weighted negative prediction is defined as the sum of weights whose corresponding classifiers predict a label of $C_0$ on testing sample x. The principle behind the learning machine of the ensemble-based scoring system 160 is an attempt to simulate the process of real-world decision making. Since the present disclosure addresses the parameters and classifier analysis as binary class problems, the presentation of risk score calculation can be simplified in accordance with the following equation.

$$RS_x = \frac{\sum_{t=1}^{T} \varphi_t(x, L) \cdot w_t}{\sum_{t=1}^{T} w_t} \times 100 \quad (4)$$

Further, in the present disclosure, it is desired to determine how to select suitable individual classifiers to create a decision ensemble and also to determine a useful methodology for decision combinations. Addressing the above is difficult for most medical scenarios where databases are usually imbalanced, i.e., positive samples are much less than negative samples. For example in predicting acute cardiac complications, there are less than 5% positive samples amongst the past patient data. In this present disclosure, two embodiments for the ensemble-based scoring system are proposed—a first system adapting an under-sampling method to calculate a risk score, and a second system including a hybrid-sampling algorithm.

Ensemble-Based Scoring System 1—USS

Figure 4B:
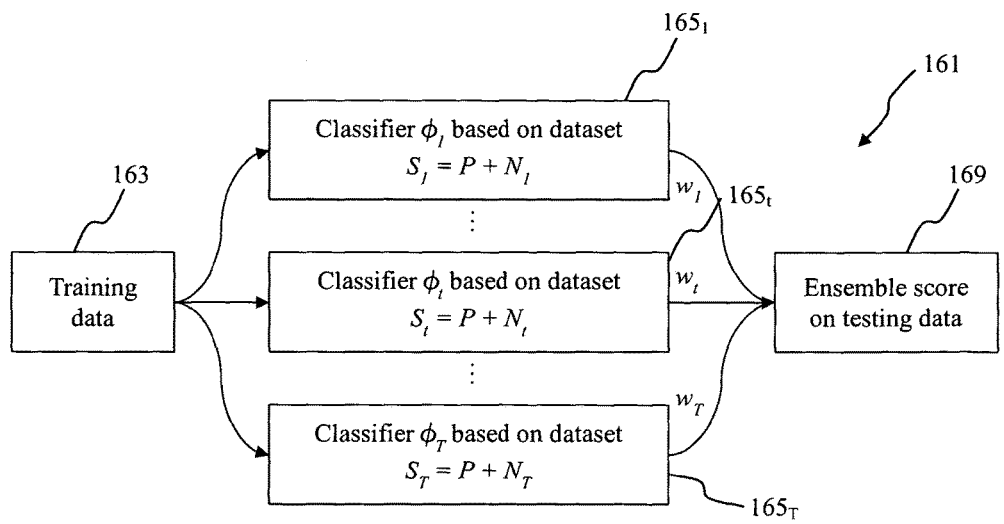
FIG. 4B illustrates a first scoring system utilizing an under-sampling method to calculate a risk score.

FIG. 4B illustrates a first scoring system utilizing an under-sampling method to calculate a risk score. In the embodiment, the ensemble-based scoring system 160 is an under-sampling based scoring system (USS) 161 where an under-sampling technique is applied. The USS is designed to conduct a risk score prediction on an imbalanced dataset. As a provided input, training dataset 163 (or L) provides a set of minority class samples P and a set of majority class samples N, and also a determined number of individual classifiers T. t is determined to be a reference to the determined classifiers $165_t$, where t=1, ..., T.

In the embodiment, the under-sampling method randomly samples a subset $N_t$ from N where $|N_t|<|N|$. In most medical scenarios, $|P|<<|N|$ such that $|N_t|=|P|$ is selected, where P represents a set of samples with positive outcomes and N represents a set of samples with negative outcomes. The resultant samples are combined to provide a balanced dataset S, where $S_t=P+N_t$.

Thereafter, the USS randomly samples T subsets and trains T independent classifiers with $N_t$ and P for each classifier $S_t$. A classification model $S_t$ is thereafter built. More detailed information on building a suitable classification model can be referenced from the article entitled "An Intelligent Scoring System and Its Application to Cardiac Arrest Prediction" (Nan LIU et al, Nov. 2012, IEEE Transactions on Information Technology in Biomedicine) by an inventor as to the present disclosure, the article being incorporated fully by reference in this present disclosure. This classification model $S_t$ is then applied onto the incoming testing sample x from testing data 166 to produce a prediction output $\phi_t(x, S_t)$ that is either 0 or 1.

In the present embodiment, it is assumed that all T individual classifiers equally contribute to the decision making and the weightage value of the classifier $\phi_t$ has a $w_t$ value as set to 1. In other embodiments, the weightage value of each classifier $\phi_t$ may be evaluated and thereafter provided with a value which reflects the importance of the parameter or classifier towards the assessment of ACS in a patient.

Several other state of the art ensemble learning methods combine the outputs of all classifiers into one composite prediction. However, in the present disclosure, it is provided where the total number of positive predictions, as well as negative predictions are calculated, and equation (4) is used to estimate a risk score, i.e. a risk score is predicted for x with: $RS_x = (\sum_{t=1}^{T} \phi_t(x,S_t) \cdot w_t / \sum_{t=1}^{T} w_t) \times 100$. This risk score is provided as an output or ensemble score 169 of the USS 161.

In this present disclosure, a support vector machine (SVM) is provided as an individual classifier in the ensemble learning based scoring system. SVM implements a conceptually simple idea, i.e. input vectors are non-linearly mapped to a high-dimensional feature space in which a linear decision hyperplane is constructed to separate input vectors with maximum margin.

Figure 5A:
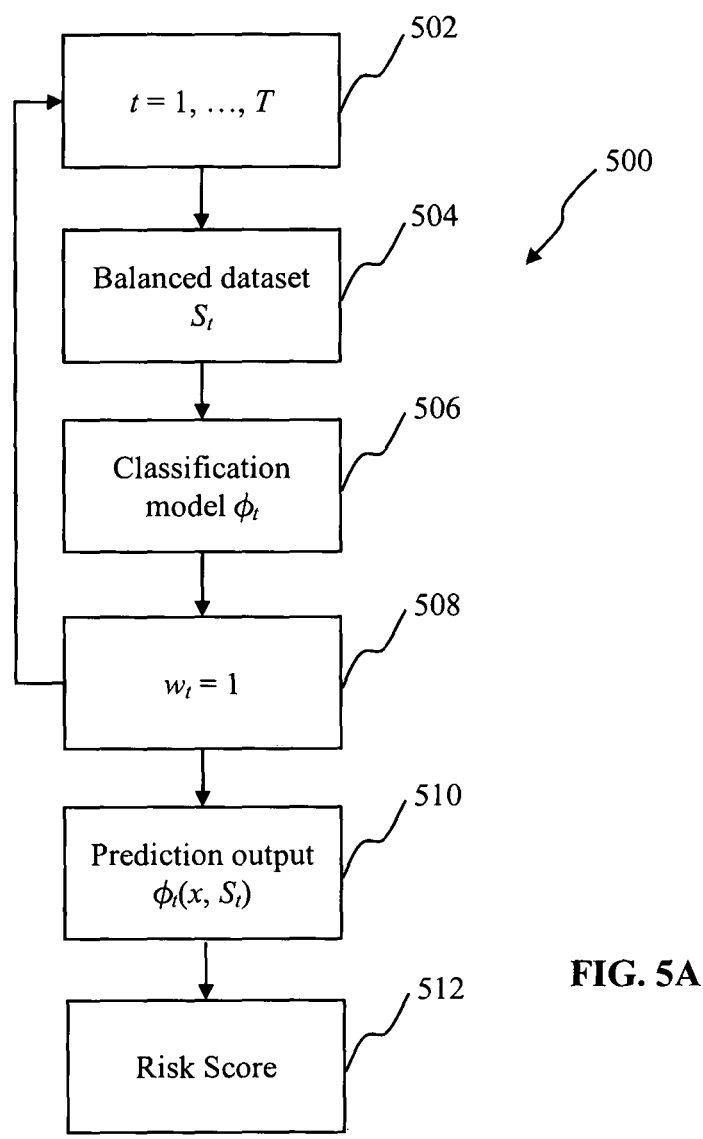
FIG. 5A is a block diagram of an algorithm of the under-sampling based scoring system.

FIG. 5A is a block diagram 500 of an algorithm of USS 161. In a first process block 502 of the present embodiment, t is determined to be a reference to the determined classifiers $165_t$, where t=1, ..., T. In a second process block 504, a balanced dataset $S_t$ is first created by combining P and $N_t$, where $N_t$ is randomly sampled from N, and where P and $N_t$ have the same number of samples.

In a next process block 506, a classification model $\phi_t$ is built based on $S_t$. In process block 508, it is assumed that all T individual classifiers are equally contributing to the decision making and the value of $w_t$ is set to 1.

Process blocks 502 to 508 are then repeated to obtain all classification models $\phi_t$, and corresponding to them each $w_t$ set to 1. In a process block 510, the classification models are applied to incoming testing sample x to obtain prediction outputs $\phi_t(x, S_t)$ that are either 0 or 1.

In a following block 512, a risk score is predicted for incoming testing data x with equation (4): $RS_x = (\sum_{t=1}^{T} \phi_t(x, S_t) \cdot w_t / \sum_{t=1}^{T} w_t) \times 100$. This risk score is provided as an output or ensemble score 169 of the USS 161.

Ensemble-Based Scoring System 2—HSS

Figure 4C:
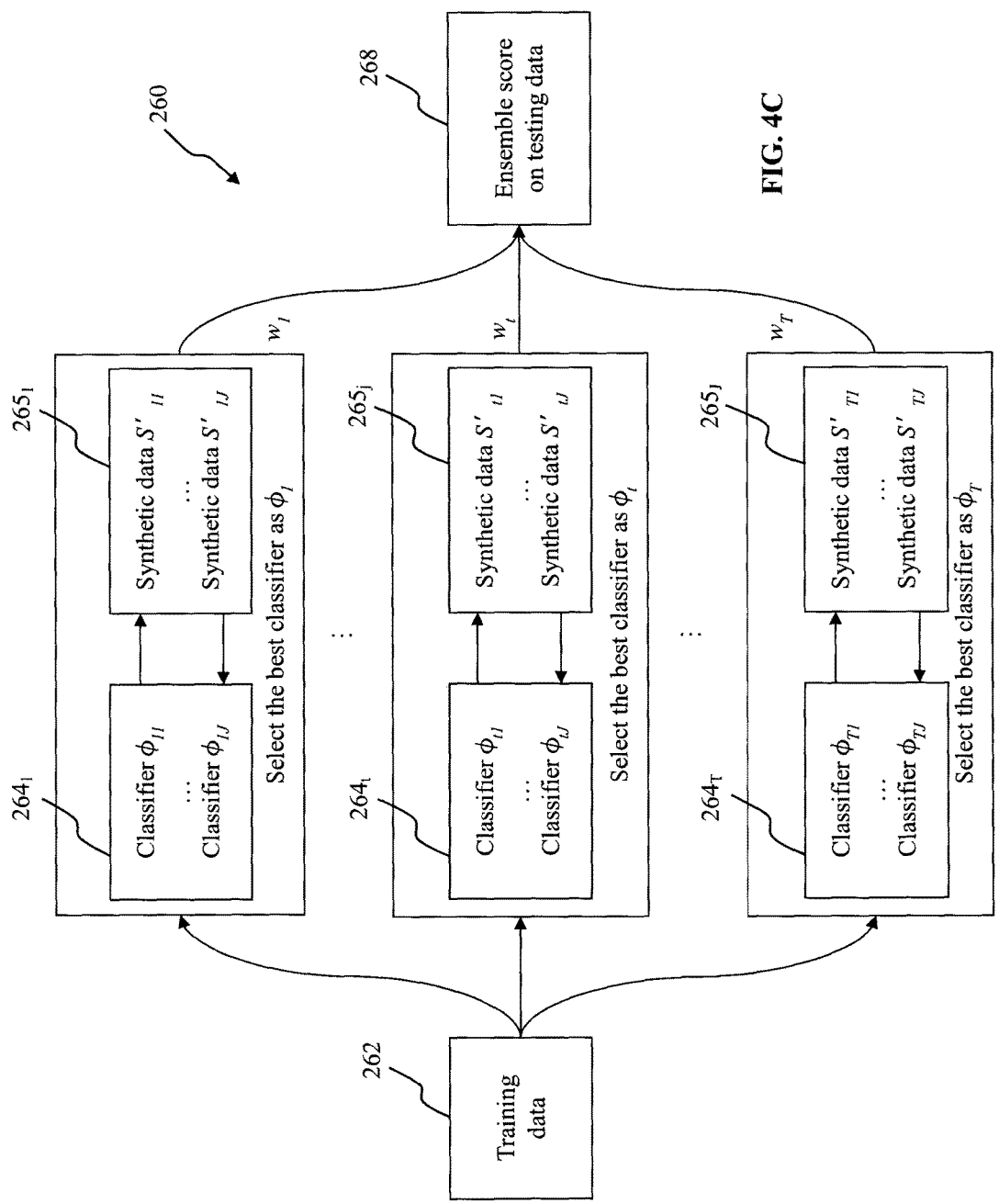
FIG. 4C illustrates a second scoring system utilizing a hybrid-sampling approach according to a second embodiment.

FIG. 4C illustrates a second scoring system utilizing a hybrid-sampling approach according to a second embodiment. In the above USS 161, random under-sampling is used for subset selection in the majority class samplings. The selection process utilized in system USS 161 provides an unsupervised strategy to explore a majority class of the data samples, i.e., the performance of each individual classifier may not be determinable, even though some of the individual classifiers may contribute less to the decision ensemble. Therefore, in a second embodiment, there is provided a supervised strategy for individual classifier selection such that a robust decision ensemble with strong discriminatory power can be built.

In the embodiment, the ensemble-based scoring system is a hybrid-sampling based scoring system (HSS) 260 where both under-sampling and over-sampling techniques are applied. State of the art intelligent machine learning systems typically utilize over-sampled data to enhance training. In this present embodiment, an over-sampling technique is used to generate synthetic data for validating individual classifiers, so as to provide a hierarchy for selecting the more relevant classifiers to create the decision ensemble.

Input is similarly provided, where training dataset 262 provides a set of minority class samples P and a set of majority class samples N, where |P|<<|N|. There is also a determined number of individual classifiers T, and a number of individual classifiers for optimization J. T and J are independent variables. T defines the ensemble size and J defines the number of classifiers for optimization. Each classifier is chosen out of J classifiers to create an ensemble containing T classifiers.

Figure 5B:
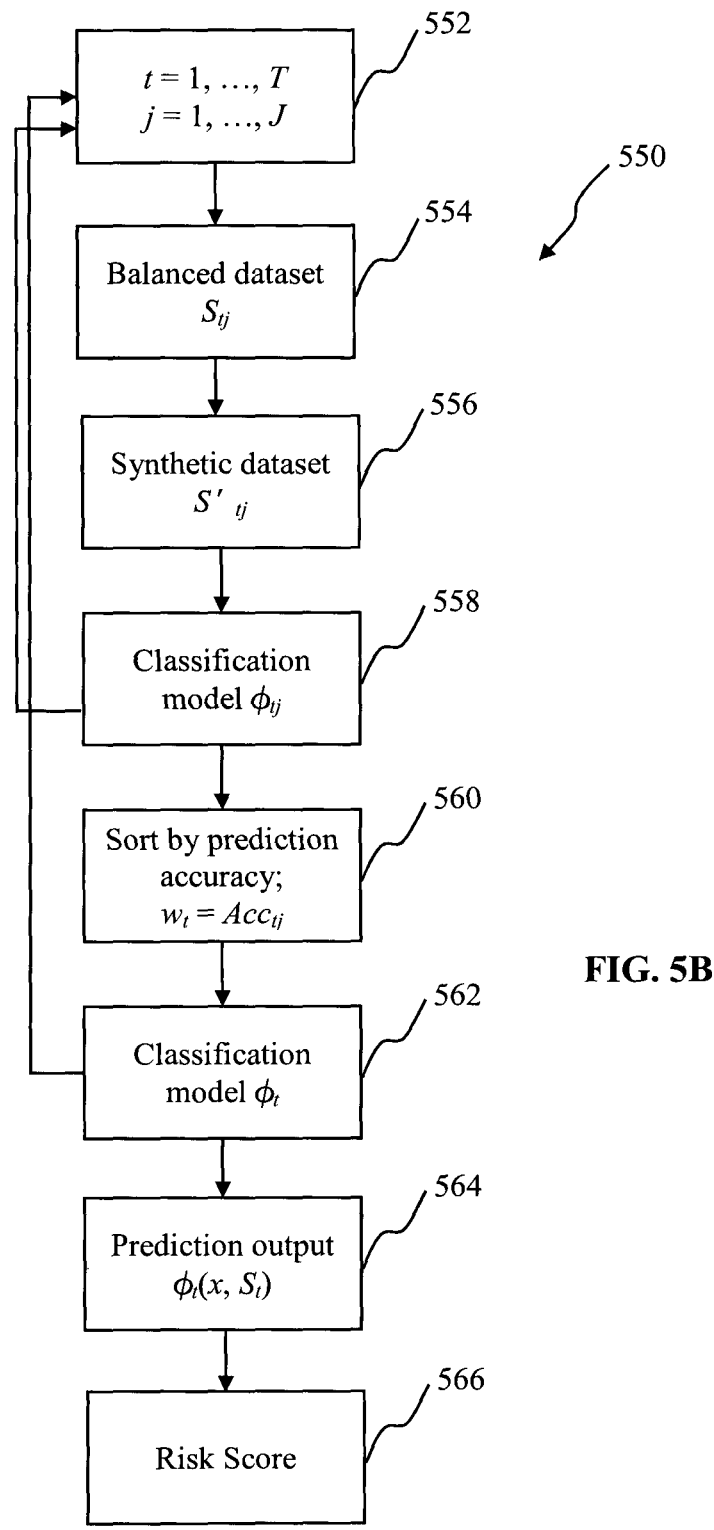
FIG. 5B is a block diagram of an algorithm of the hybrid-sampling based scoring system.

FIG. 5B is a block diagram 550 of an algorithm of HSS 260. In a first process block 552 of the present embodiment, t is determined to be a reference to the determined classifiers $264_t$, where t=1, . . . T, and j is determined to be a reference to the determined optimized classifiers 265, where j=1, . . . , J. In a second process block 554, a balanced dataset $S_{tj}$ is first created by combining P and $N_{tj}$, where $N_{tj}$ is randomly sampled from N, and where P and $N_{tj}$ have the same number of samples.

In a following process block 556, a synthetic dataset $S_{tj}$ is created by combining P and $N_{tj}$, where P is obtained by applying SMOTE on P and $N_{tj}$ is obtained by applying SMOTE on $N_{tj}$. SMOTE stands for Synthetic Minority Over-sampling Technique, and is used in the art for the construction of classifiers from imbalanced datasets.

In SMOTE, the class data set, typically the minority class, is over-sampled by taking each data sample and introducing synthetic examples along a line segment joining any/all of a k sample class nearest neighbors, where k is a predetermined variable based on the amount of over-sampling required. For example, if the amount of over-sampling required is 200%, only 2 neighbors from the 5 nearest neighbors are chosen and one sample is generated in the direction of each. In generating the synthetic sample, a random number is provided between 0 and 1, which is thereafter multiplied with and added to the sample vector under consideration. This provides a selection of a random point along the line segment between two specific features, and effectively allows the decision region of the class data set to become more general, typically in discussion of the minority class in comparison with the majority class.

SMOTE provides the addition of synthetic samples which cause the classifiers to create larger and less specific decision regions, rather than smaller and more specific region. The overall result is such that decision trees generalize better. In the embodiment, both data sets P and $N_{tj}$, where both sets include a number of samples equal to the minority class set, are applied with SMOTE to obtain a new synthetic dataset $S_{tj}$, where $S_{tj}=P+N_{tj}$.

In a next process block 558, a classification model $\phi_{tj}$ is built based on $S_{tj}$, and the trained model $\phi_{tj}$ is validated based on $S_{tj}$. The resultant prediction accuracy of the classification model $\phi_{tj}$ is stored as $Acc_{tj}$.

Process blocks 552 to 558 are then repeated to obtain the prediction accuracy of each classification model, until all J classifiers for optimization have been processed.

In a process block 560, the dataset $S_{tj}$ with the highest prediction accuracy $Acc_{tj}$ is selected as the first balanced dataset as $S_1$ and its weightage $w_1$ is set as corresponding prediction accuracy $Acc_{tj}$.

In a following process block 562, a classification model $\phi_1$ is built/trained based on $S_1$ and the trained classification model $\phi_1$ is applied to incoming testing sample x to produce a prediction output $\phi_1(x, S_1)$ that is either 0 or 1. In another embodiment, the previously built classification model for which the prediction accuracy was obtained for is reused.

Process blocks 552 to 562 are then repeated to obtain the prediction output of each weighted and sorted classification models $\phi_t$, until all T classifiers have been processed. In particular, the balanced datasets are sorted in the order $S_1$, $S_2$, . . . , $S_t$, . . . , $S_T$, each with a corresponding weightage $w_1$, $w_2$, . . . $w_t$, . . . $w_T$, based on the earlier obtained prediction accuracy. The corresponding classification models $\phi_1, \phi_2, \ldots, \phi_t, \ldots, \phi_T$, are built based on the balanced datasets and thereafter applied to incoming testing sample x to obtain prediction outputs $\phi_t(x, S_t)$ that are either 0 or 1 in a process block 564.

In a process block 566, a risk score is predicted for incoming testing data x with equation (4): $RS_x=(\Sigma_{t=1}^{T}\phi_t(x, S_t)\cdot w_t / \Sigma_{t=1}^{T} w_t) \times 100$. This risk score is provided as an output or ensemble score 268 of the HSS 260.

To further describe the embodiment, a weighted decision ensemble can be created to predict risk scores on incoming testing sample x. An advantage of the HSS 260 is its unique strategy for classifier selection, which is a supervised process that takes the performance of an individual classifier into account.

As mentioned previously, there is an intention to introduce an alternative way of using over-sampled data, i.e., for validation instead of training. In the HSS 260, a classifier $264_1$ is trained with $S_{tj}$ and validated with $S_{tj}$, and the validation accuracy $Acc_{tj}$ is recorded as a weightage to indicate the importance of the classifier. A higher $Acc_{tj}$ value indicates that the individual classifier $\phi_{tj}$ would be able to contribute more to the decision ensemble. Thus, the dataset $S_{tj}$ with the highest $Acc_{tj}$ is selected and sorted in order as $S_1$, $S_2, \ldots, S_t, \ldots, S_T$, with a corresponding weightage wt set with the previously obtained validation accuracy $Acc_{tj}$ as its value. The classifier $\phi_t(x, S_t)$ is then built or trained for ensemble creation, and derivation of the ensemble score is similarly provided from equation (4).

Several advantages of utilizing HSS 260 as the ensemble-based scoring system of the present disclosure have been identified, and are provided as follows.

The present disclosure utilizes at least or up to 13 parameters derived from the 12-lead ECG, at least or up to 16 HRV parameters and at least or up to 8 vital signs for a risk score prediction. These parameters have been selected based on an understanding that 12-lead ECG parameters combined with HRV parameters would be able to provide a more accurate prediction as compared to a scoring system based on a single type of feature. Furthermore, the proposed HSS 260 as the ensemble-based scoring system 160 is flexible as applied to real-world scenarios; it is not limited to above-mentioned parameters as inputs. Based on clinical needs, any number of parameters can be fed into the scoring system HSS 260 for risk prediction if they are found to be able to achieve required prediction performance.

However, to accommodate various types of inputs, the system needs to be retrained. The present HSS 260 provides a flexibility in retraining, without compromising the quality of the risk score output. A retraining would take into account each classifier, validates the classification model for each classifier and sorts each classifier, including the new parameter/classifier based on the validation accuracy or relevant importance of each parameter/classifier.

The proposed scoring system HSS 260 also has the flexibility of model retraining to handle different conditions such as changes of input features and changes of prediction targets. The scoring system adopts a machine learning structure, and thus includes an effective model training strategy to deal with potential changes within a trained model. For example, if a subset of features is preferred in risk prediction, simply re-running the proposed scoring system with these new features would then generate an entirely new model. A training requirement would of course be that provided training samples from accumulated past patient data and incoming testing samples must have the same input parameters for assessment. Having the flexibility of retraining, the proposed system can be easily implemented regardless of diseases and demographics. As long as clinically meaningful predictors are collected, any disease under any demographics can be predicted. Satisfactory performance could be achieved given that the study is well designed and the collected data is accurate. For example, a well-trained prediction model for Asian population may not work well in American population.

Applicable to both USS 161 and HSS 260, the pre-assessment learning to build up classification models for risk score prediction allows the scoring system 160 and thus the triage system 100 to be free from additional processing load, for example, if the scoring system required a live identification of relevant input parameter and constant access to the past patient data. In the present disclosure, the triage system 100 can be a standalone system, without need for access to a centralized data server 108 to obtain past patient data. There could be multiple advantages of such a feature, for example, in providing a triage system for use in a mass casualty event, or even in mobile hospitals operating without standard emergency department resource allocation.

Central Processing—USS

Figure 6:
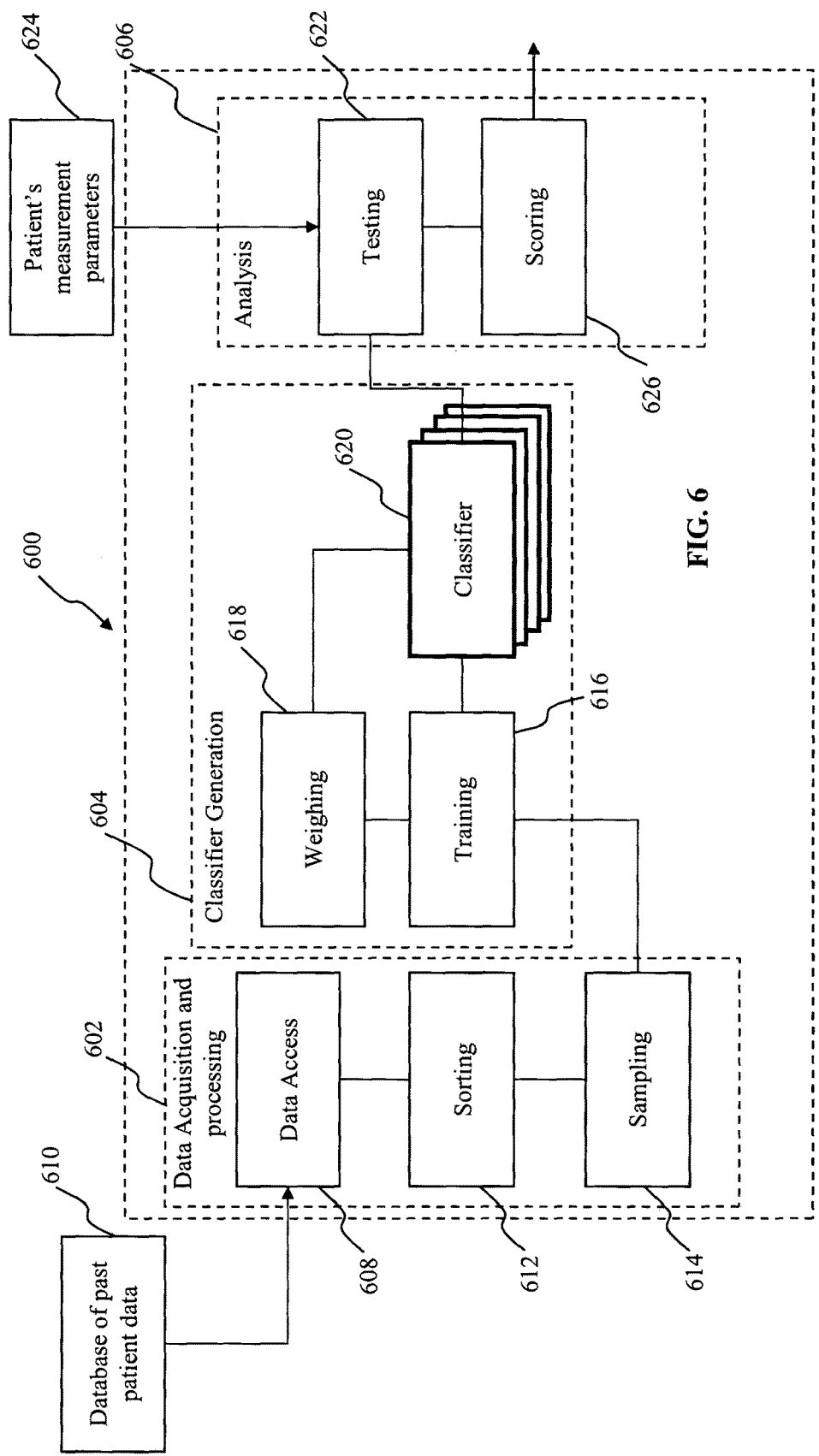
FIG. 6 illustrates a modular layout of an ensemble-based scoring system of the triage system according to an embodiment.

FIG. 6 illustrates a modular layout of an ensemble-based scoring system of the triage system according to an embodiment. In the embodiment, USS 161 is provided as the ensemble-based scoring system, and is designed to operate as an application program based in a memory module of the central processor 104, and operating on the central processor 104. As indicated, "module" as described refers to the particular function or functions performed by the associated processing unit; and the "module" may or may not correspond to actual electrical circuitry.

In general, the USS 161 includes 3 larger functional modules as indicated in the modular layout 600—a data acquisition and processing module 602, a classifier generation module 604, and an analysis module 606. Functionally, the data acquisition and processing module 602 supervises the request and receipt of accumulated past patient data through a data access module 608 from a database 610 that, in the present embodiment, is hosted on a centralized data server 108, and apart from the central processor 104 of the triage system 100. In an embodiment, the provided data communication link between data access module 608 and the database 610 is a wireless communication link, for example in accordance with WLAN protocol IEEE 802.11a-ad. An on-demand access is provided for communication between the data access module 608 and the database 610, but a perpetual access situation can also be provided.

Data access module 608 obtains from the database 610 information relating to previous patients, in particular, groups of data as sorted by a unique identifier, in this case, a patient name or an identity registration number. Critically, the outcome of the patient's visit to the ED is also included and obtained. The data groups obtain include a plurality of various parameters relating to the functional purpose of the scoring system 160, the assessment of a risk score in relation to the risk of ACS of an incoming patient. The parameters as obtained may be the parameters listed in the above description, that of medical status, physiological data, ECG parameters, and HRV parameters. Alternatively, other parameters as decided as necessary may be obtained.

After past patient data has been obtained by the data access module 608, the data is provided onto a sorting module 612 for further processing. Sorting module 612 separates each parameter for assessment, as decided by the triage system 100, from the group of data as uniquely identified, and puts them into parametrically sorted datasets. The sorting module 612 further tags each processed parameter with the unique identifier of each patient it belongs to, as well as the outcome of the patient's trip to the hospital. Typically, the resultant parametrically sorted datasets are imbalanced datasets, where there exists a majority class with normal data, in this case a negative outcome, and a minority class with abnormal data, in this case a positive outcome.

After sorting, the sorted data is provided to a sampling module 614, wherein the sampling module 614 identifies a majority class or dataset of the provided imbalanced dataset, the majority class including a first number of data samples, and a minority class or dataset including a second smaller number of data samples. The sampling module 614 thereafter extracts a subset of a third number of data samples from the majority data set, such that the number of samples of the majority data subset is equal to that of the minority data dataset. This provides for balanced datasets of parameters relating to classifiers. In the embodiment, the extraction of the majority data subset is entirely random.

The balanced datasets are thereafter provided to a training module 616, where data received by the USS 161 is trained into classifiers such that incoming patient data may be received and evaluated against the trained classifier to provide a portion of a risk assessment score as to the health of a patient. In training module 616, the balanced dataset is used to build a classification model, where the classification model, or classifier acts as an expert in providing an insight on whether the incoming patient is likely to have a positive outcome in relation to ACS.

In the present embodiment, after the classification models are built by the training module 616, the models are provided to a weighing module 618. In the present embodiment, it is assumed that all of the classifiers provide an equal contribution to the decision making and as such, the weighing module 618 provides all the classifiers with an equal weight of 1. In other embodiments, the weightage value of each classifier may be evaluated and thereafter provided with a value which reflects the importance of the parameter or classifier towards the assessment of ACS in a patient. This value would then be provided to the classifier by the weighing module 618.

An output of the classifier generation module 604 is thus that of trained classifiers 620, related to the various parameters indicated as being of importance toward the assessment of a risk score by the triage system 100. Preferably, the classifiers 620 are sorted according to their weight or importance. However, in this embodiment, this is not carried out as the weightage of each classifier has been set to 1.

The USS 161 is now ready for usage and assessment of an incoming patient, and for providing a risk score therefrom. Analysis module 606 includes a testing module 622 arranged to receive incoming patient test data 624 from the central processor 104 of the present triage system 100. In this embodiment, each received parameter of the incoming patient test data 624 is tested with a corresponding trained classifier 620 to provide a prediction output of whether the patient is likely to achieve a negative or positive outcome. The prediction output is provided in a binary output format of 0 or 1.

After testing and evaluation of all the parameters and classifiers, the resultant prediction outputs are collated and passed on to a scoring module 626. Scoring module 626 calculates the risk score for the incoming patient, based on his incoming measurement parameters 624, as a normalized summation of the binary prediction outputs of all the weighted classifiers. This generated risk score provides the medical personnel using the triage system 100 with a calibrated insight as to whether the incoming patient is at a risk of ACS.

Central Processing—HSS

Figure 7:
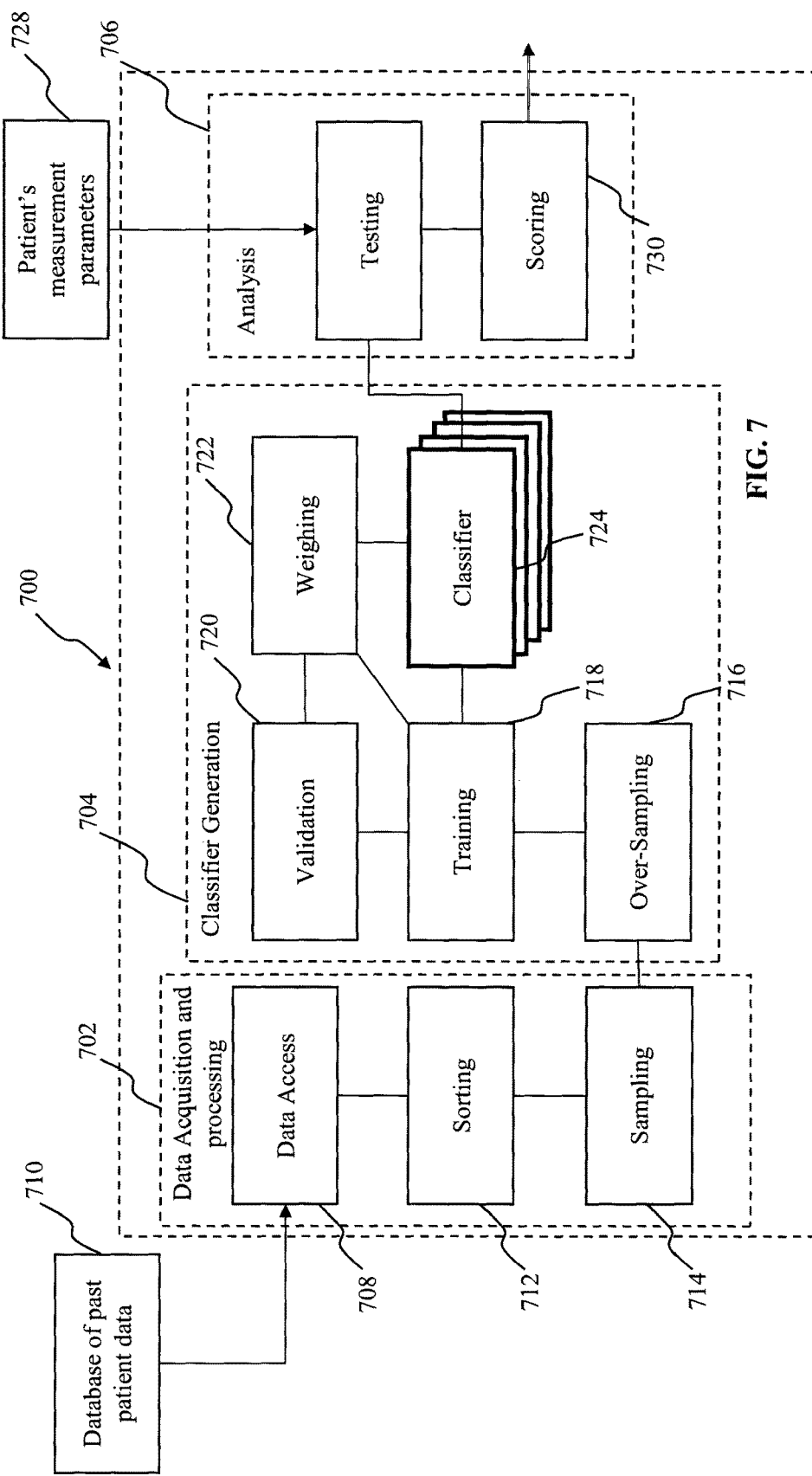
FIG. 7 illustrates a modular layout of an ensemble-based scoring system of the triage system according to a second embodiment.

FIG. 7 illustrates a modular layout of an ensemble-based scoring system of the triage system according to a second embodiment. In the embodiment, the HSS 260 is provided as the ensemble-based scoring system, and is designed to operate as an application program based in a memory module of the central processor 104, and operating on the central processor 104. As indicated, "module" as described refers to the particular function or functions performed by the associated processing unit; and the "module" may or may not correspond to actual electrical circuitry.

In general, the HSS 260 includes 3 larger functional modules as indicated in the modular layout 700—a data acquisition and processing module 702, a classifier generation module 704, and an analysis module 706. Functionally, the data acquisition and processing module 702 supervises the request and receipt of accumulated past patient data through a data access module 708 from a database 710 that, in the present embodiment, is hosted on a centralized data server 108, and apart from the central processor 104 of the triage system 100. In an embodiment, the provided link between data access module 708 and the database 710 is a wireless communication link, for example in accordance with WLAN protocol IEEE 802.11a-ad.

Data access module 708 obtains from the database 710 information relating to previous patients, in particular, groups of data as sorted by a unique identifier, in this case, a patient name or an identity registration number. Critically, the outcome of the patient's visit to the ED is also included and obtained. The data groups obtain include a plurality of various parameters relating to the functional purpose of the scoring system 160, the assessment of a risk score in relation to the risk of ACS of an incoming patient. The parameters as obtained may be the parameters listed in the above description, that of medical status, physiological data, ECG parameters, and HRV parameters. Alternatively, other parameters as decided as necessary may be obtained.

After past patient data has been obtained by the data access module 708, the data is provided onto a sorting module 712 for further processing. Sorting module 712 separates each parameter for assessment, as decided by the triage system 100, from the group of data as uniquely identified, and puts them into parametrically sorted datasets. The sorting module 712 further tags each processed parameter with the unique identifier of each patient it belongs to, as well as the outcome of the patient's trip to the hospital. Typically, the resultant parametrically sorted datasets are imbalanced datasets, where there exists a majority class with normal data, in this case a negative outcome, and a minority class with abnormal data, in this case a positive outcome.

After sorting, the sorted data is provided to a sampling module 714, wherein the sampling module 714 identifies a majority class or dataset of the provided imbalanced dataset, the majority class including a first number of data samples, and a minority class or dataset including a second smaller number of data samples. The sampling module 714 thereafter extracts a subset of a third number of data samples from the majority data set, such that the number of samples of the majority data subset is equal to that of the minority data dataset. This provides for balanced datasets of parameters relating to classifiers. In the embodiment, the extraction of the majority class subset is entirely random.

The balanced datasets, i.e. the majority data subset and the minority dataset, are thereafter provided to an oversampling module 716, where a process of synthetic over-sampling with replacement (SMOTE) is carried out on the first majority data subset and the minority data set to create a synthetic data set. In carrying out SMOTE, the over-sampling module 716 takes a data point in the first minority data set and introduces synthetic examples along a line segment joining the data point to a predetermined number of data point neighbors. A synthetic data set is formed with reference to both the majority data subset and the minority dataset.

A training module 718 is provided, where data received by the HSS 260 is trained into classifiers such that incoming patient data may be received and evaluated against the trained classifier to provide a portion of a risk assessment score as to the health of a patient. In training module 718, the balanced dataset is used to build a classification model, where the classification model, or classifier acts as an expert in providing an insight on whether the incoming patient is likely to have a positive outcome in relation to ACS.

After the classification models have been built, one classifier for each parameter under analysis, the classification models are provided to a validation module 720. Validation module 720 carries out a validation of each classification model by running its corresponding synthetic dataset through the classification model so as to obtain a resultant prediction accuracy of the classification model, which represents the importance of the classifier. Each classification model is thus provided with its prediction accuracy, after the validation module 720 has validated the classification model with its corresponding synthetic dataset.

In the present embodiment, after the classification models are validated by the validation module 720, the models are provided to a weighing module 722. Weighing module 722 carries out a sorting function on the classification models based on its validation accuracy and arranges them in order, from highest to lowest, i.e. most important to least important. The weighing module thereafter provides a weightage value to each sorted classification model, set as its corresponding prediction accuracy. In the present embodiment, after the classification sorting by validation accuracy, a rebuild of the classification model is carried out with its corresponding dataset. In another embodiment, the previously built classification model for which the prediction accuracy was obtained for is reused.

An output of the classifier generation module 704 is thus that of trained, validated and weighed classifiers 724, related to the various parameters indicated as being of importance toward the assessment of a risk score by the triage system 100.

The HSS 260 is now ready for usage and assessment of an incoming patient, and for providing a risk score therefrom. Analysis module 706 includes a testing module 726 arranged to receive incoming patient test data 728 from the central processor 104 of the present triage system 100. In this embodiment, each received parameter of the incoming patient test data 728 is tested with a corresponding trained classifier 724 to provide a prediction output of whether the patient is likely to achieve a negative or positive outcome. The prediction output is provided in a binary output format of 0 or 1.

After testing and evaluation of all the parameters and classifiers, the resultant prediction outputs are collated and passed on to a scoring module 730. Scoring module 730 calculates the risk score for the incoming patient, based on his incoming measurement parameters 728, as a normalized summation of the binary prediction outputs of all the weighted classifiers. This generated risk score provides the medical personnel using the triage system 100 with a calibrated insight as to whether the incoming patient is at a risk of ACS.

Clinical Validation

A clinical study was carried out by the present applicants as to the validity of the presently disclosed triage system for use in emergency departments of hospitals in generating a risk score in assessing incoming patients for acute coronary syndromes. An observational cohort study of 564 critically ill patients with undifferentiated non-traumatic chest pain was conducted from March 2010 to March 2012. Patients were comprised of a convenience sample presenting to the ED of Singapore General Hospital, the main acute tertiary hospital in Singapore, serving 135,000 patients annually. Ethics approval with a waiver of patient consent was obtained from the Institutional Review Board. In this study, recruited patients were adult men and women at least 30 years of age who presented to the ED with a primary complaint of non-traumatic chest pain. Patients in non-sinus rhythm (e.g. asystole, supraventricular and ventricular arrhythmias, complete heart block) and patients who were discharged against medical advice or transferred to another hospital within 72 hours of arrival at the ED were excluded. An eligible patient who arrived at the ED with chest pain was randomly screened and recruited by trained medical personnel.

The primary outcome was a composite of severe complications within 72 hours of arrival at the ED, extracted from the electronic hospital records. Patients were considered to have met the outcome if they had at least one of the following severe complications: all-cause mortality, cardiac arrest, sustained ventricular tachycardia (VT), hypotension requiring inotropes or intra-aortic balloon pump (IABP) insertion, intubation or mechanical ventilation, complete heart block, and bradycardia requiring insertion of a pacing wire. In the compiled database, 19 out of 564 patients met the primary outcome.

Evaluation of the scoring system is based on the leave-one-out cross-validation (LOOCV) framework. In a dataset of K samples, K iterations are required for algorithm evaluation. Within iteration, one sample is used as the testing sample while the rest samples are used for training. The proposed score prediction process needs to repeat K times so that each sample can be tested individually. Having the risk scores for the entire dataset, a proper threshold is derived to report sensitivity and specificity.

TABLE 1

Confusion matrix used for defining TP, TN, FP and FN

|  | Predicted acute cardiac complications within 72 h | Predicted health |
|---|---|---|
| Actual acute cardiac complications within 72 h | TP | FN |
| Actual health | FP | TN |

Table 1 shows a confusion matrix table used for defining true positive (TP), false positive (FP), true negative (TN), and false negative (FN). TP indicates patients with acute cardiac complications within 72 h correctly predicted as acute cardiac complications within 72 h; FP indicates healthy patients incorrectly predicted as cardiac arrest within 72 h; TN indicates healthy patients correctly predicted as healthy; and FN indicates patients with acute cardiac complications within 72 h incorrectly predicted as healthy. Thereafter, calculations for the sensitivity and the specificity of the system are provided as follows:

$$\text{Sensitivity} = \frac{TP}{TP + FN} \quad (5)$$

$$\text{Specificity} = \frac{TN}{TN + FP} \quad (6)$$

Further, the receiver operation characteristic (ROC) curve, the positive predictive value (PPV) and the negative predictive value (NPV) are also used to present system performance, where PPV and NPV are defined as:

$$PPV = \frac{TP}{TP + FP} \quad (7)$$

$$NPV = \frac{TN}{TN + FN} \quad (8)$$

A prospective, non-randomized, observational study to assess the utility of combining 12-lead ECG, HRV and vital signs as a predictor of acute cardiac complications within 72 hours was conducted based on a cohort of 564 patients with chest pain attended at the Department of Emergency Medicine, Singapore General Hospital. USS and HSS algorithms using 12-lead ECG, HRV and vital signs achieved area under the ROC curve (AUC) of 0.799 and 0.813, respectively, which were superior to both TIMI score (AUC of 0.621) and MEWS score (AUC of 0.672). The comparison results in Table 2 and FIG. 6 have shown the effectiveness of the proposed scoring systems in the prediction of acute cardiac complications. The cutoff scores were selected to keep both sensitivity and specificity as high as possible. Note that the ranges of scores for USS and HSS are 0-100 and the ranges of scores for TIMI and MEWS are 0-6. We observe that PPV values are small while NPV values are large, which is due to the fact of imbalanced data where negative class is the majority class. It is worth noting that both USS and HSS algorithms are able to filter out 99% patients without acute cardiac complications, and this capability is useful to conducting triage in critically ill patients. Furthermore, both USS and HSS can pick up 78.9% patients who met the primary outcomes, and meanwhile maintain high specificities (>73%).

TABLE 2

Prediction results with different scoring methods where inputs are feature vectors consisting of 12-lead ECG, HRV and vital signs

| Scoring method | Cutoff Score | AUC (95% CI) | Sensitivity (95% CI) | Specificity (95% CI) | PPV (95% CI) | NPV (95% CI) |
|---|---|---|---|---|---|---|
| USS | 36.7 | 0.799 (0.677-0.920) | 78.9% (60.6%-97.3%) | 73.6% (69.9%-77.3%) | 9.4% (4.9%-14.0%) | 99.0% (98.0%-100.0%) |
| HSS | 50.6 | 0.813 (0.694-0.931) | 78.9% (60.6%-97.3%) | 74.1% (70.5%-77.8%) | 9.6% (5.0%-14.2%) | 99.0% (98.1%-100.0%) |
| TIMI | 1.0 | 0.621 (0.484-0.757) | 78.9% (60.6%-97.3%) | 36.7% (32.7%-40.7%) | 4.2% (2.1%-6.2%) | 98.0% (96.1%-99.9%) |
| MEWS | 1.0 | 0.672 (0.537-0.808) | 42.1% (19.9%-64.3%) | 78.5% (75.1%-82.0%) | 6.4% (2.9%-10.7%) | 97.5% (96.0%-99.0%) |

Figure 8A:
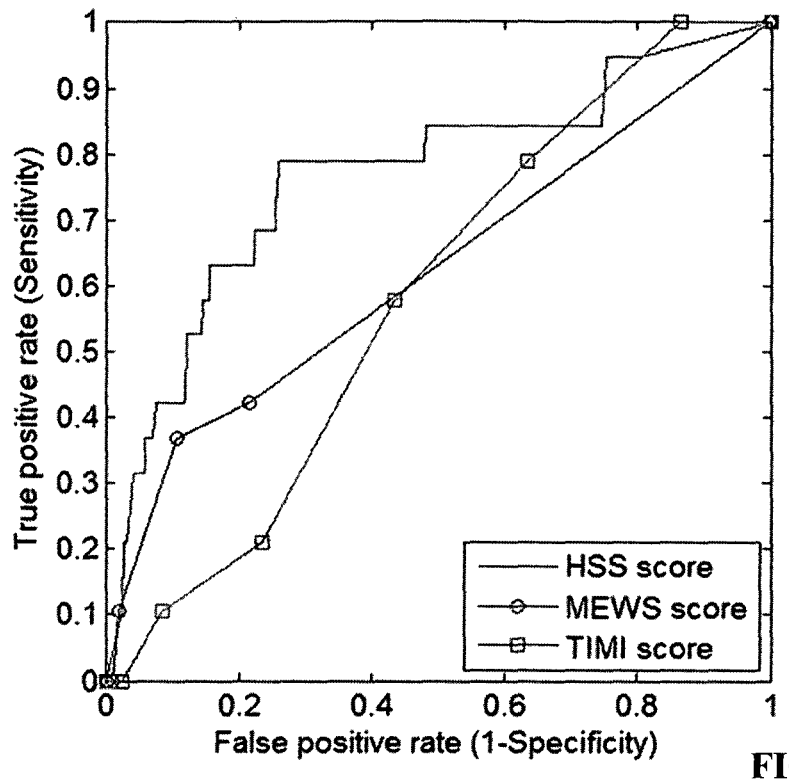
FIG. 8A charts the performance of USS vs. TIMI and MEWS.
Figure 8B:
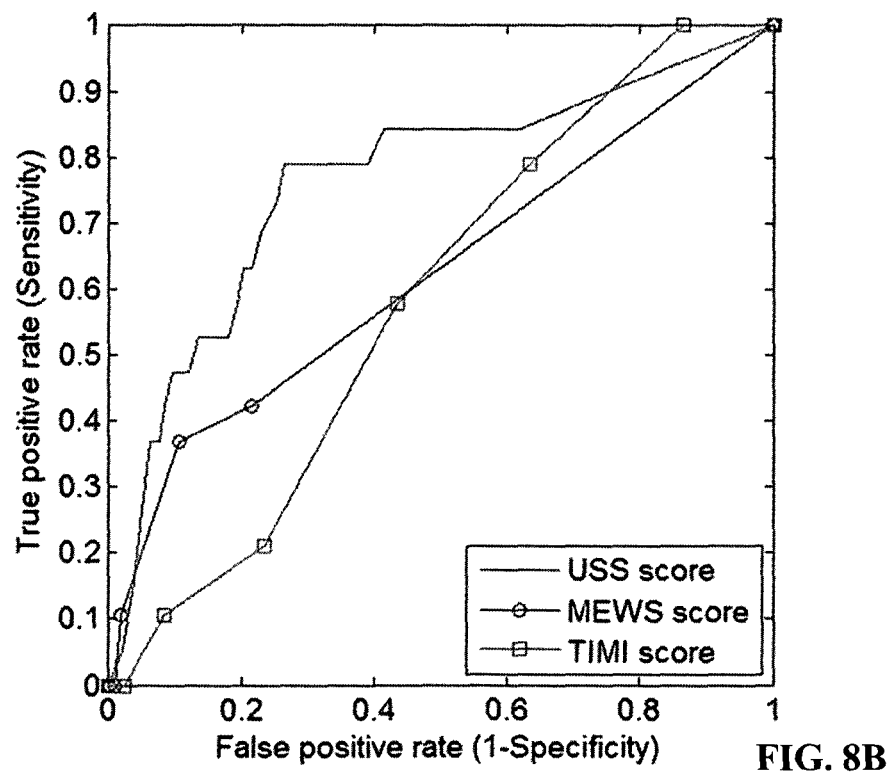
FIG. 8B charts the performance of HSS vs. TIMI and MEWS.

In the ROC analysis, we compared USS and HSS to both TIMI score and MEWS score separately and recorded the comparison results in FIG. 8A and FIG. 8B, respectively. FIG. 8A charts the performance of USS vs. TIMI and MEWS. FIG. 8B charts the performance of HSS vs. TIMI and MEWS. In general, both proposed USS and HSS outperformed TIMI and MEWS in terms of achieving higher AUC, sensitivity, specificity, PPV and NPV values.

Figure 9A:
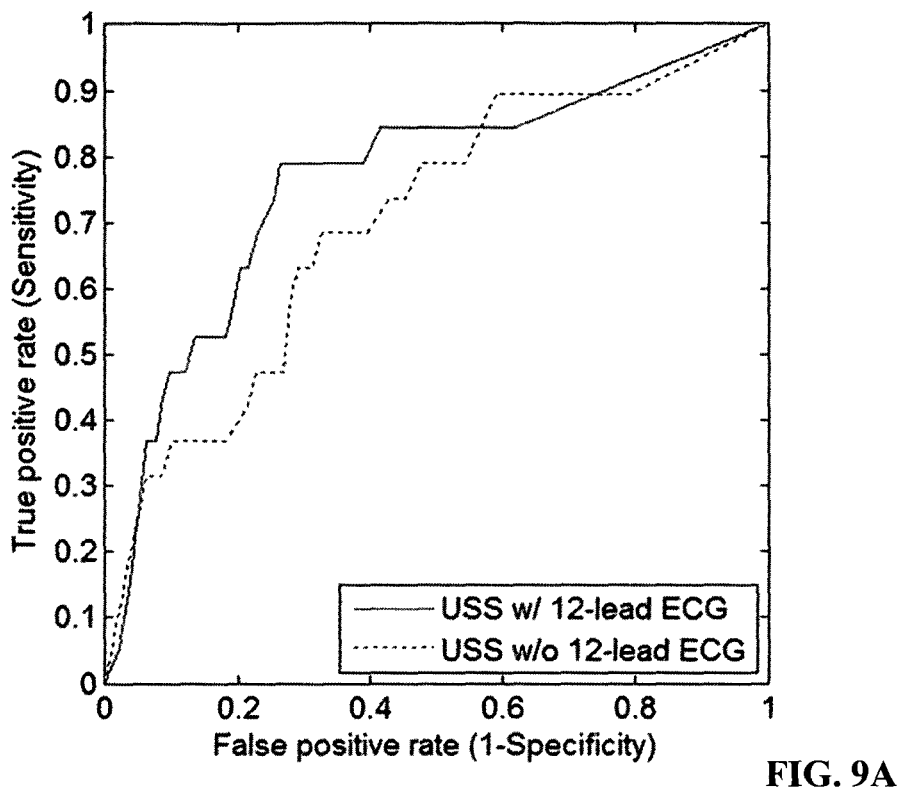
FIG. 9A charts the performance of USS with and without 12-lead ECG parameters.
Figure 9B:
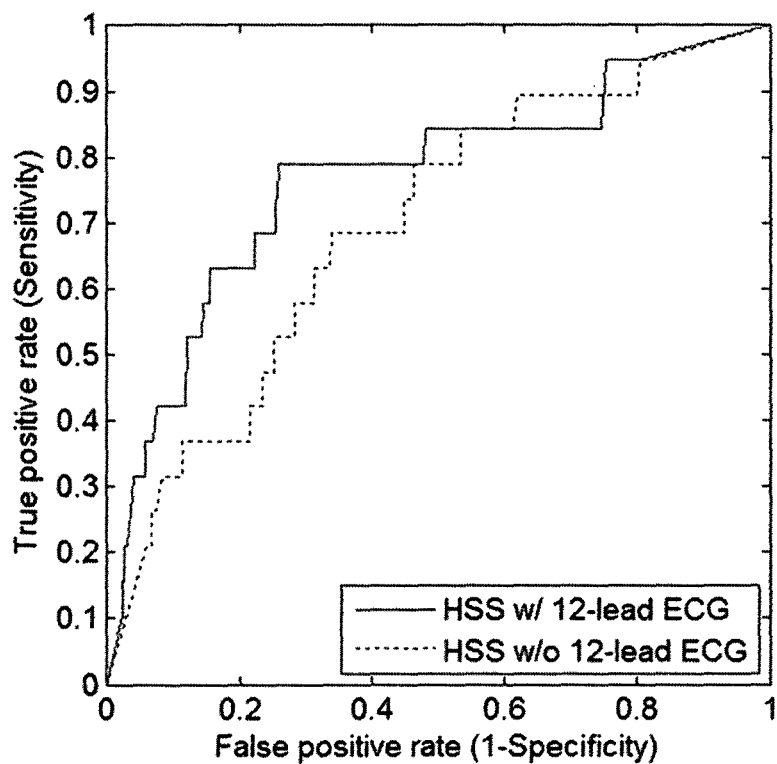
FIG. 9B charts the performance of HSS with and without 12-lead ECG parameters.

In the present disclosure, an intelligent triage system with a novel scoring system to integrate 12-lead ECG, HRV and vital signs for risk prediction is described. An investigation was thus also carried out to determine how the 12-lead ECG contributes to the system. Evaluations were conducted on features with and without 12-lead ECG parameters with USS and HSS algorithms and the comparison results are presented in Table 3 and FIG. 9A and FIG. 9B. FIG. 9A charts the performance of USS with and without 12-lead ECG parameters. FIG. 9B charts the performance of HSS with and without 12-lead ECG parameters. Compared to the scoring methods with 12-lead ECG parameters, it is observed that methods without 12-lead ECG parameters achieved lower AUC, specificity, PPV, and NPV values. In other words, 12-lead ECG may be a significant predictor of acute cardiac complications.

alternatively, be used for carrying out a determination of a risk score of a patient under any other circumstance, within the scope of the present disclosure.

For example, an embodiment is envisioned wherein a cardiac event assessment system is provided for home or other (e.g. office) use. The home-use cardiac event assessment system would include a generally central ensemble-based scoring system, which is envisioned as a portable assessment system, configured for ease of use without a trained medical practitioner. Such a system would be limited such that a cardiac event risk score is provided as the assessment output, the risk score providing an insight as to severity of any present chest pain, and for encouraging home users to take the relevant medical action.

Such a system is envisioned to include data connectivity to the internet and thereafter establish a secure data connection with the hospital past patient data database. Classifiers in the scoring system of the cardiac event assessment system are pre-built for the home-user, such that in the event of use, a result can be provided more expediently.

In home use, vital signs such as heart rate, respiratory rate, blood pressure, or $SpO_2$ readings can be taken and provided as input to the cardiac event assessment system. Further, to provide an even more accurate present diagnosis an ECG

TABLE 3

Results of different scoring methods with and without 12-lead ECG parameters

| Scoring method | Cutoff Score | AUC (95% CI) | Sensitivity (95% CI) | Specificity (95% CI) | PPV (95% CI) | NPV (95% CI) |
|---|---|---|---|---|---|---|
| USS (w/ ECG) | 36.7 | 0.799 (0.677-0.920) | 78.9% (60.6%-97.3%) | 73.6% (69.9%-77.3%) | 9.4% (4.9%-14.0%) | 99.0% (98.0%-100.0%) |
| USS (w/o ECG) | 20.0 | 0.729 (0.598-0.860) | 78.9% (60.6%-97.3%) | 52.3% (48.1%-56.5%) | 5.5% (2.8%-8.1%) | 98.6% (97.3%-100.0%) |
| HSS (w/ ECG) | 50.6 | 0.813 (0.694-0.931) | 78.9% (60.6%-97.3%) | 74.1% (70.5%-77.8%) | 9.6% (5.0%-14.2%) | 99.0% (98.1%-100.0%) |
| HSS (w/o ECG) | 33.4 | 0.730 (0.599-0.861) | 78.9% (60.6%-97.3%) | 53.8% (49.6%-57.9%) | 5.6% (2.9%-8.4%) | 98.7% (97.3%-100.0%) |

In addition, upon reviewing further the results reported in Table 2 and Table 3, it was found that both USS and HSS still outperformed TIMI and MEWS scores even though 12-lead ECG was not used for prediction. This observation provided more evidence on the effectiveness of the proposed USS and HSS algorithms in predicting acute cardiac complications.

Although the following description of particular system embodiments is directed at a triage system 100 for determining a risk score in a hospital emergency department, it will be understood that the system 100 according to various embodiments of the present disclosure can additionally, or can be taken, where the results can be analyzed with an ECG analysis module and an ECG parameter and/or a HRV parameter provided to the cardiac event assessment system. Analysis can thus be carried out quickly against the pre-built classifiers and a risk score as to a cardiac event can be provided.

In home use, another embodiment is envisioned wherein the cardiac event assessment system is provided for home use. The home-use cardiac event assessment system includes an emergency alarm system. In the event of an emergency where the risk score goes beyond a pre-built acceptable risk score provided to the cardiac event assessment system, the emergency alarm system will trigger an alarm and with internet connectivity or 3G or 4G or Wifi, the alarm will transfer the risk score to the trained medical practitioner who is holding a portable handheld device capable of receiving the risk score. The trained medical practitioner can then immediately return to the hospital and provide evasive rescue to the patient.

Aspects of particular embodiments of the present disclosure address at least one aspect, problem, limitation, and/or disadvantage associated with existing hospital ED triage systems. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope and spirit of the present disclosure. Such different systems, components, processes and/or modifications, alterations, and/or improvements are encompassed by the following claims.

The invention claimed is:

1. A system for determining a risk score for triage, comprising:
a first input device for measuring a first input parameter relating to physiological data of a patient, the first input parameter comprising a vital signs parameter;
a twelve-lead electrode electrocardiogram (ECG) device, for carrying out a electrocardiography procedure on the patient, and establishing an ECG obtained from results of the electrocardiography procedure, the ECG device comprising an ECG extraction module to extract at least one ECG parameter from the ECG;
a heart rate variability (HRV) analysis module for determining a HRV analysis from the ECG, the HRV analysis comprising at least one HRV parameter; and
an ensemble-based scoring system, comprising:
a plurality of weighted classifiers for providing a risk score calculation, the plurality of weighted classifiers established based on past patient data in a database of accumulated past patient data;
a sorting module arranged to:
receive data from the database of accumulated past patient data; and
sort the data into a plurality of data sets, each data set corresponding to a classifier, and comprising an imbalanced data set;
a sampling module arranged to:
receive a first imbalanced data set corresponding to a first classifier comprising a first majority data set comprising a first number of data samples, and a first minority data set comprising a second number of data samples, from the sorting module; and
extract a first majority data subset comprising a third number of samples from the first majority data set, wherein the third number of samples in the first majority data subset is equal to the second number of samples in the first minority data set; and
an analysis module for receiving the first input parameter, the at least one HRV parameter, and the at least one ECG parameter which are communicated or transmitted to the ensemble-based scoring system, wherein the analysis module determines a risk score by comparing the first input parameter, the at least one HRV parameter, and the at least one ECG parameter to corresponding weighted classifiers.

2. The system for determining a risk score as claimed in claim 1, wherein the ensemble-based scoring system further comprises a data access module for obtaining past patient data and configured for data communication with the database of accumulated past patient data.

3. The system for determining a risk score as claimed in claim 1, wherein the ensemble-based scoring system further comprises a classifier generation module for establishing the plurality of weighted classifiers, based on past patient data provided by the data access module.

4. The system for determining a risk score as claimed in claim 3, wherein the classifier generation module further comprises a training module arranged to:
receive the first majority data subset and the first minority data set from the sampling module; and
build a first classification model to represent the first classifier with the first majority data subset and the first minority data set.

5. The system for determining a risk score as claimed in claim 4, wherein the training module receives a plurality of majority data subsets and minority data sets from the sampling module; and builds classification models representing a plurality of classifiers with the received plurality of majority data subsets and minority data sets.

6. The system for determining a risk score as claimed in claim 1, wherein the ensemble-based system further comprises an over-sampling module arranged to:
receive the first majority data subset and the first minority data set from the sampling module; and
create a first synthetic data set by applying a process of synthetic over-sampling with replacement on the first majority data subset and the first minority data set.

7. The system for determining a risk score as claimed in claim 6, wherein the ensemble-based system further comprises a validation module arranged to:
build a first classification model with a training module based on the first majority data subset and the first minority data set corresponding to the first classifier;
validate the first classification model against the first synthetic data set; and
obtain a resultant prediction accuracy of the first classification model, representing the importance of the first classifier.

8. The system for determining a risk score as claimed in claim 7, wherein the over-sampling module receives a plurality of majority data subsets and minority data sets from the sampling module and creates a plurality of synthetic data sets;
the training module builds a plurality of classification models representing a plurality of classifiers with the received plurality of majority data subsets and minority data sets; and
the validation module validates the plurality of classification models against the plurality of synthetic data sets, and obtains a plurality of prediction accuracies of the classification models, representing the importance of each of the plurality of classifiers.

9. The system for determining a risk score as claimed in claim 8, wherein the classifier generation module further comprises a weighing module for allocating each of the plurality of classifiers with a weightage according to its importance, to obtain the plurality of weighted classifiers.

10. A method of determining a risk score, comprising:
   measuring a first input parameter relating to physiological data of a patient, the first input parameter comprising a vital signs parameter;
   carrying out a twelve-lead electrocardiography procedure on the patient;
   establishing a ECG from results of the electrocardiography procedure, the ECG comprising at least one ECG parameter extractable from the ECG;
   extracting the at least one ECG parameter from the ECG;
   determining a heart rate variability (HRV) analysis from the ECG, the HRV analysis comprising at least one HRV parameter;
   providing the first input parameter, the at least one HRV parameter, and the at least one ECG parameter to an ensemble-based scoring system, the ensemble-based scoring system comprising:
      a plurality of weighted classifiers for providing a risk score calculation, the plurality of weighted classifiers established based on past patient data in a database of accumulated past patient data;
      a sorting module arranged to:
         receive data from the database of accumulated past patient data; and
         sort the data into a plurality of data sets, each data set corresponding to a classifier, and comprising an imbalanced data set;
      a sampling module arranged to:
         receive a first imbalanced data set corresponding to a first classifier comprising a first majority data set comprising a first number of data samples, and a first minority data set comprising a second number of data samples, from the sorting module; and
         extract a first majority data subset comprising a third number of samples from the first majority data set, wherein the third number of samples in the first majority data subset is equal to the second number of samples in the first minority data set; and
      an analysis module for receiving the first input parameter, the at least one HRV parameter, and the at least one ECG parameter which are communicated or transmitted to the ensemble-based scoring system; and
   determining a risk score with the ensemble-based scoring system by comparing the first input parameter, the at least one HRV parameter, and the at least one ECG parameter to corresponding weighted classifiers.

11. The method of determining a risk score as claimed in claim 10, wherein the at least one ECG parameter is any one of a ST elevation, a T wave inversion, a Q wave, a QT interval correction (QTc), a QRS axis, a left bundle branch block (BBB), a right BBB, an IntraVentricular Conduction Delay (IVCD), a left atrial abnormality (LAA), a left ventricular hypertrophy (VH), a right VH, and an atrial fibrillation.

12. The method of determining a risk score as claimed in claim 10, comprising extracting a plurality of RR intervals from the ECG and performing any one of a time domain analysis and a frequency domain analysis to obtain the at least one HRV parameter.

13. The method of determining a risk score as claimed in claim 12, wherein the at least one HRV parameter is any one of an average length of the RR intervals, standard deviation of all RR intervals, a mean heart rate, a standard deviation of all instantaneous heart rate values, a NN50 count, a pNN50 percentage, a square root of mean squared differences of successive RR intervals, a HRV triangular index, a baseline width of triangular fit into a RR interval histogram, a total power, a very low frequency power, a low frequency power (LF), a high frequency power (HF), a normalized low frequency power, a normalized high frequency power, and a ratio of LF/HF.

14. The method of determining a risk score as claimed in claim 10, wherein the first input parameter is any one of a heart rate, a respiratory rate, a blood pressure reading, a temperature reading, a Glasgow Coma Score (GCS), an oxygen saturation reading, and a pain score.

15. The method of determining a risk score as claimed in claim 10, further comprising establishing a second input parameter relating to a medical status of the patient, providing the second input parameter to the ensemble-based scoring system, and determining the risk score by further comparing the second input parameter to a corresponding weighted classifier.

16. The method of determining a risk score as claimed in claim 15, wherein the second input parameter is any one of a medical history, a drug history, a smoking history, a family history of heart disease, and a number of angina events in the past 24 hours.

17. A method of determining a risk score for triage using a system according to claim 1, operating to process data including said first input parameter, said at least one HRV parameter, and said at least one ECG parameter, said method comprising:
   receiving a first imbalanced dataset corresponding to a first classifier and sampling the data samples to form a first balanced data set;
   creating a first synthetic data set by applying a process of synthetic over-sampling with replacement on the first balanced data set;
   building a first classification model based on the first balanced data set corresponding to the first classifier;
   validating the first classification model against the first synthetic data set; and
   obtaining a resultant prediction accuracy of the first classification model, representing the importance of the first classifier.

18. The method of determining a risk score for triage as claimed in claim 17, said method further comprising:
   obtaining a plurality of prediction accuracies relating to a plurality of classification models; sorting the plurality of classification models according to its prediction accuracy;
   allocating each of the plurality of classification models with a weightage according to its importance to obtain a plurality of said weighted classifiers; evaluating an input parameter with its corresponding weighted classifier;
   generating a binary prediction output of either 0 or 1 for each evaluated weighted classifier; and
   calculating the risk score based on a normalized summation of the binary prediction outputs of all evaluated weighted classifiers.

* * * * *

UNITED STATES PATENT AND TRADEMARK OFFICE
CERTIFICATE OF CORRECTION

PATENT NO. : 10,299,689 B2
APPLICATION NO. : 14/773747
DATED : May 28, 2019
INVENTOR(S) : Marcus Eng Hock Ong et al.

Page 1 of 1

It is certified that error appears in the above-identified patent and that said Letters Patent is hereby corrected as shown below:

In the Specification

At Columns 31-32, Lines 1-15, in TABLE 2, under the heading "PPV (95% CI)", the table entry for Scoring Method, MEWS, of "6.4% (2.9%-10.7%)", should be -- 6.4% (2.1%-10.7%) --.

Signed and Sealed this
Sixth Day of August, 2019

Andrei Iancu
*Director of the United States Patent and Trademark Office*